(12) United States Patent
Vats

(10) Patent No.: US 9,523,120 B2
(45) Date of Patent: Dec. 20, 2016

(54) METHOD OF AMPLIFYING A NUCLEIC ACID

(75) Inventor: Abhay N. Vats, Wexford, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 14/125,450

(22) PCT Filed: Jun. 14, 2012

(86) PCT No.: PCT/US2012/042374
§ 371 (c)(1),
(2), (4) Date: Jan. 30, 2014

(87) PCT Pub. No.: WO2012/174192
PCT Pub. Date: Dec. 20, 2012

(65) Prior Publication Data
US 2014/0329702 A1 Nov. 6, 2014

Related U.S. Application Data

(60) Provisional application No. 61/496,620, filed on Jun. 14, 2011.

(51) Int. Cl.
*C12Q 1/68* (2006.01)
*C12Q 1/70* (2006.01)
*C07H 21/02* (2006.01)

(52) U.S. Cl.
CPC .............. *C12Q 1/686* (2013.01); *C12Q 1/689* (2013.01); *C12Q 1/6853* (2013.01); *C12Q 1/701* (2013.01)

(58) Field of Classification Search
CPC ....... C12Q 1/6853; C12Q 1/686; C12Q 1/689; C12Q 1/701
See application file for complete search history.

(56) References Cited

U.S. PATENT DOCUMENTS

| | | |
|---|---|---|
| 8,093,030 B2 | 1/2012 | Schoenfeld et al. |
| 2008/0182312 A1 | 7/2008 | Pack et al. |
| 2009/0047678 A1 | 2/2009 | Kutyavin |
| 2009/0130677 A1 | 5/2009 | Kim et al. |
| 2012/0171673 A1* | 7/2012 | Nakamura ........... C12Q 1/6809 435/6.11 |

FOREIGN PATENT DOCUMENTS

| | | | | |
|---|---|---|---|---|
| WO | 2011003690 A1 | | 1/2011 | |
| WO | WO 2011/001496 | * | 1/2011 | ........... C12Q 1/6809 |

OTHER PUBLICATIONS

Grankvist, O. et al., J. Virol. Meth., vol. 62, pp. 131-141 (1996).*
Curtis, K.A. et al., J. Virol. Meth., vol. 151, pp. 264-270 (2008).*
Kouguchi, Y. et al., Mol. Cell. Probes, vol. 24, pp. 190-195 (Mar. 2010).*
Li, J-S. et al., J. Med. Virol., vol. 45, pp. 151-155 (1995).*
Fahy et al., Self-sustained sequence replication (3SR): an isothermal transcription-based amplification system alternative to PCR, Genome Research, 1991, pp. 25-33, Issue 1.
Pavlov et al., Helix-hairpin-helix motifs confer salt resistance and processivity on chimeric DNA polymerases, Proceedings of the National Academy of Sciences of the United States of America, Oct. 15, 2002, pp. 13510-13515, vol. 99, No. 21.
University of Pittsburgh, Spiral DNA Replication (SPIDR): A novel isothermal DNA amplification method, iBridge Network, generated on Aug. 7, 2014, 2 pages.
Van Der Vliet et al., Nucleic acid sequence-based amplification (NASBA) for the identification of mycobacteria, Journal of General Microbiology, 1993, pp. 2423-2429, Issue 139.
Walker, Empirical aspects of strand displacement amplification, Genome Research, 1993, pp. 1-6, Issue 3.

* cited by examiner

*Primary Examiner* — Teresa Strzelecka
(74) *Attorney, Agent, or Firm* — The Webb Law Firm

(57) ABSTRACT

A nucleic acid amplification method is provided, along with kits useful in performing the amplification method.

17 Claims, 13 Drawing Sheets

HIV B/C

OUTER-F
GAAGGCTTTTAGCCCAGAAGTAATACCCATGTTTTCAGCGTTATCAGAAG

INNER-R
GAGCCACCCCACAAGATTTAAACACCATGCTAAACACAGT---GGGGGGA

CATCA---AGCAGCCATGCAAATATTAAAAGATACCATCAATGAAGAGGC

TGCAGAATGGGATAGATTACATCCAGTACATGCAGGGCCTATTGCACCAG

INNER-F
GCCAAATGAGAGAACCAAGGGGAAGTGACATAGCAGGAACTACTAGTAAC

OUTER-R
CTACAGGAACAAATAGCATGGATGACGAGTAACCCACCTGTTCCAGTAGG

AGACATCTATAAAAGATGGATAATTCTGGGATTAAATAAAATAGTAAGAA

Fig. 6A

DENGUE

OUTER-F
ACCGTGCTGCCTGTAGCTCCGCCAATAACGGGAGGCGTTAAATTCCCAGGGAGGCCATGCGCCACGGAAGC

INNER-R
TGTGCGCGTGGCATATTGGACTAGCGGTTAGAGGAGACCCCTCCCATCACCAACAAAACGCAGCAAAAAAG

GGGGCCCGAAGCCAGGAGGAAGCTGTACTCCTGGTGGAAGGACTAGAGGTTAGAGGAGACCCCCCCAACAC

Loop B
AAAAACAGCATATTGACGCTGGGAAAGACCAGAGATCCTGCTGTCTCTACAACATCAATCCAGGCACAGAG

OUTER-R
CGCCGCGAGATGGATTGGTGTTGTTGATCCAACAGGTTCT

Fig. 6B

WEST NILE VIRUS

```
                                                            OUTER-F
AAGCTTGGAGAATATGGAGAGGTGACAGTGGACTGTGAACCACGGTCAGGGATTGACACCAATGCATACTA

INNER-R
CGTGATGACTGTTGGAACAAAGACGTTCTTGGTCCATCGTGAGTGGTTCATGGACCTCAACCTCCCTTGGA

GCAGTGCTGGAAGTACTGTGTGGAGGAACAGAGAGACGTTAATGGAGTTTGAGGAACCACACGCCACGAAG

Loop B
CAGTCTGTGATAGCATTGGGCTCACAAGAGGGAGCTCTGCATCAAGCTTTGGCTGGAGCCATTCCTGTGGA

OUTER-R
ATTTTCAAGCAACACTGTCAAGTTGACGTCGGGTCATTTGAAGTGTAGAGTGAAGATGGAAAAATT
```

Fig. 6C

INFLUENZA VIRUS A (H1N1, H3N2 AND H5N1) M1 REGION

```
                 OUTER-F
ATATTGAAAGATGAGTCTTCTAACCGAGGTCGAAACGTACGTTCTCTCTATCGTCCCGTCAGGCCCCCTCA

INNER-R
AAGCCGAGATCGCACAGAGACTTGAAGATGTCTTTGCTGGAAAGAACACCGATCTTGAGGCTCTCATGGAA

Loop B
TGGCTAAAGACAAGACCGATCCTGTCACCTCTGACTAAGGGGATTTTAGGATTTGTGTTCACGCTCACCGT

OUTER-R
GCCCACTGAGCGAGGACTGCATCGTACACTCTTTGTCCAAAATGCCCTTAATGGGAATGGGGATCCAAATA

ATATGGACAGAGCAGTTAAACTGTATAGAAAGCTTAAGAGGGAGATAACATTCCATGGGGCCAAAGAAATA
```

Fig. 6D

INFLUENZA VIRUS B M1 REGION

OUTER-F
<u>TATGTCGCTGTTTGGAGACAC</u>AATTGCCTACCTGCTTTCATTGACAGAAGATGGAGAAGGCAAAGCAGAACTAGCAGAA

INNER-R
AAATTACACTGTTGGTTTGGTGGGAAAGAATTT<u>GACCTAGACTCTGCCTTGGA</u>ATGGATAAAAAACAAAAGATGCTTAA

CTGATATACAAAAAGCACTAATTGGTGCCTCTATATGCTTTTTAAAACCCAAAGACCAGGAAAGAAAAAGAAGATTCAT

CACAGAGCCCTTATCAGGAATGGGAACAACAGCAACAAAAAAGAAAGGCCTGATTCTGGCTGAGAGAAAAATGAGAAGA

Loop B
TGTGTGAGCTTTCATGAAGCATTT<u>GAAATAGCAGAAGGCCATG</u>AAAGCTCAGCGCTACTATACTGTCTCATGGTCATGT OUTER-R
ACCTGAATCCTGGAAATTATTCAAT<u>GCAAGTAAAACTAGGAACGCTC</u>

Fig. 6E

E COLI

GAAACACCATACCAACGCCACGTTCTGCTGGCGGAGTGTCATTCATCCGTTTCTCACCGA

OUTER-F
TGAACAGGTCGCCG<u>CTGGTGATCGTCTCAAGCCCGG</u>CAATCATGCGCAGTAAAGTCGATT

TACCGCAGCCAGACGGTCCGACAAACACCACGAATTCACCTTCATGGATATCGAGATTGA

INNER-R                               INNER-F
TATCTTTCG<u>ATACCACGACCTCGCCCCAGGCTTTCGTTA</u><u>CATTTTGCAGCTGTACGC</u>TCG

CCATGCCCTTCTCCCTTTGTAACAACCTGTCATCGACAGCAACATTCATGATGGGCTGAC

TATGCGTCATCAGGAGATGGCTTAAATCCTCCACCCCCTAGCTTTTTTATGGGGGAGGAG

OUTER-R
<u>GCGGGAGGATGAGAACGCGG</u>CTTCTGTGA

Fig. 6F

KLEBSIELLA

```
    OUTER-F
AAACTGATTGGTCTGCCGGCGCCGGTAGGCATGCTGTTCCTCGCGGTACTGTTAAAGCTGGCTAACGTGGTG

INNER-R                                      INNER-F
TCTCCGCGTCTGCAGGAGGGGTCGCAGATGGTGTATAAATTCTTCCGCACCGCGGTCACCTACCCGATCCTCTTT

OUTER-R
GCCGTCGGCGTGGCGATCACTCCGTGGCAGGAACTGGTAAACGCCTTCACTTTAACCAACCTGCTGGTGA

TCGTC
```

Fig. 6G

CHLAMYDIA

```
AAGTTAGACGAAATTTTGTCTTTGCGCACAGACGATCTATTTTTTGCATCCAATCAGATTTCCTTTCGCATTAAAAA
AAGACAGAATAAAGAAACCAAAATTCTAATCACATTTCCTATCAGCTTAATGGAGGAGTTGCAAAAATACACTTGTG
GGAGAAATGGGAGAGTATTTGTTTCTAAAATAGGGATTCCTGTAACAACAAGTCAGGTTGCGCATAATTTTAGGCTT
GCAGAGTTCTATAGTGCTATGAAAATAAAAATTACTCCTAGAGTACTTCGTGCAAGCGCTTTGATTCATTTAAAGCA
AATAGGATTAAAAGATGAGGAAATCATGCGTATTTCCTGTCTTTCATCGAGACAAAGTGTGTGTTCTTATTG

TTCTGGGGAAGAGGTAAGTCCTCTAGTACAAACACCCCCAATATTGTGATATAATTAAAATTATATTCATATTCTGT
TGCCAGAAAAAACACTTTTAGGCTATATTAGAGCCAATCTTCTTTGAAGCGTTGTCTTCTCGAGAAGATTTATCGTA
CGCAAATAT

OUTER-F
CATCTTTGCGGTTGCGTGTCCTGTGACCTTCATTATGTCGGAGTCTGAGCACCCTAGGCGTTTGTACTCCG
                INNER-R
TCACAGCGGTTGCTCGAAGCACGTGCGGGGTTATCTTAAAAGGGATTGCAGCTTGTAGTCCTGCTTGAGAG
                   INNER-F                                      OUTER-R
AACGTGCGGGCGATTTGCCTTAACCCCACCATTTTTCCGGAGCGAGTTACGAAGACAAAACCTCTTCGTTG

ACCGATG

TACTCTTGTAGAAAGTGCATAAACTTCTGAGGATAAGTTATAATAATCCTCTTTTCTGTCTGACGGTTCTTAAGCTG
GGAGAAAGAAATGGTAGCTTGTTGGAAACAAATCTGACTAATCTCCAAGCTTAAGACTTCAGAGGAGCGTTTACCTC
CTTGCAGCATTGTCTGGGCGATCAACCAATCCCGGGCATT
```

Fig. 6H

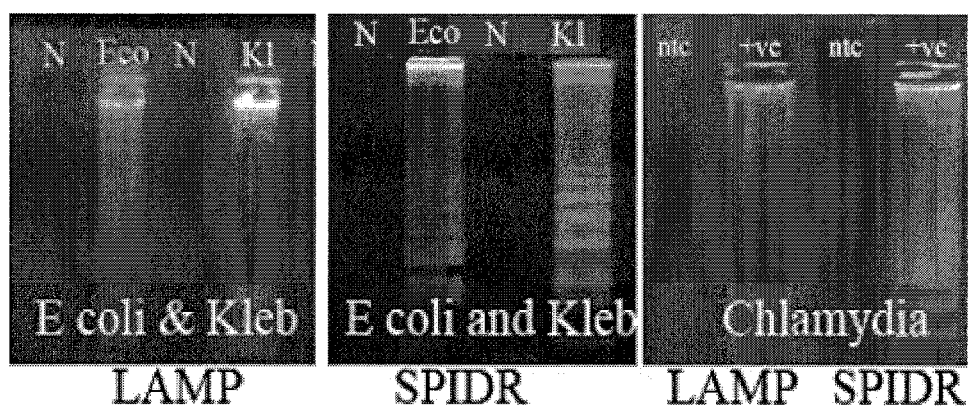
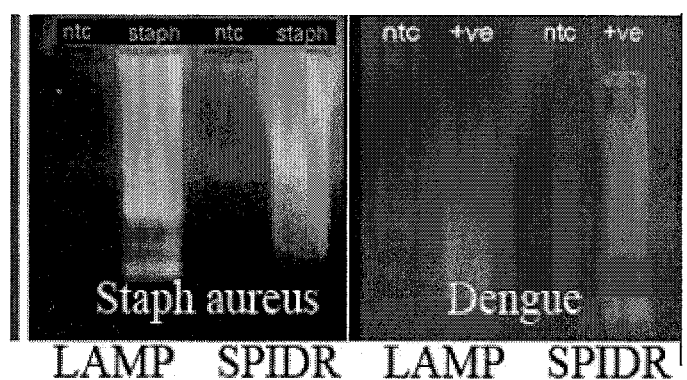
Fig. 7

```
      SPR-O-F              SPR-I(F/R)-1
GCCATCTCCTGATGACGCATAGTCAGCCCATCATGAATGTTGCTGTCGAT
                    SPR-I(R/F)-2
GACAGGTTGTTACAAAGGGAGAAGGGCATGGCGAGCGTACAGCTGCAAA
                        SPR-I(F/R)-3
ATGTAACGAAAGCCTGGGGCGAGGTCGTGGTATCGAAAGATATCAATCTC
                                              SPR-O-R
GATATCCATGAAGGTGAATTCGTGGTGTTTGTCGGACCGTCTGGCTGCGGTAAAT
```
*Fig. 8*
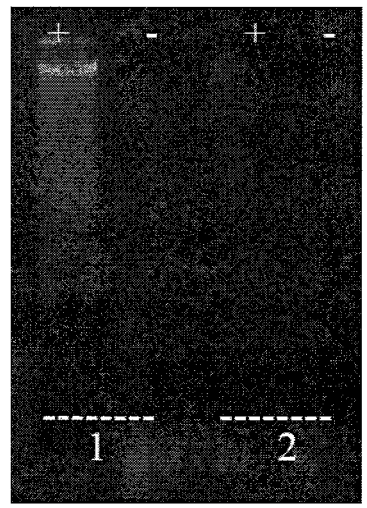
*Fig. 9*
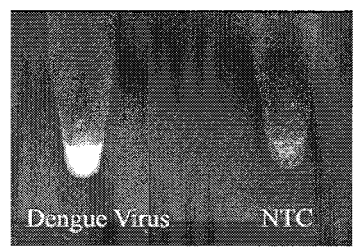
*Fig. 10*

```
                        SP3-OF                              SP3-IR
TGCACTTTCTACAAGAGTACATCGGTCAACGAAGAGGTTTTGTCTTCGTAACTCGCTCCGGAAAAATGGT

SP3-ITP-F
GGGGTTAAGGCAAATCGCCCGCCCGCACGTTCTCTCAAGCAGGACTACAAGCTGCAATCCCTTTTAAGAT

SP3-ITP-R                           SP3-IF
AACCCCGCACGTGCTTCGAGCAACCGCTGTGACGGAGTACAAACGCCTAGGGTGCTCAGACTCCGACATA

SP3-OR
ATGAAGGTCACAGGACACGCAACCGCAAAGATG
```

METHOD OF AMPLIFYING A NUCLEIC ACID

CROSS REFERENCE TO RELATED APPLICATIONS

This application is a National Stage of International Patent Application No. PCT/US2012/042374, filed Jun. 14, 2012, which claims the benefit of U.S. Provisional Application No. 61/496,620, filed Jun. 14, 2011, entitled "Nucleic Acid Amplification Method," each of which is incorporated herein by reference in its entirety.

STATEMENT REGARDING FEDERAL FUNDING

This invention was made with government support under Grant Nos. RR024153 and AI082614, awarded by the National Institutes of Health. The government has certain rights in the invention.

The Sequence Listing associated with this application is filed in electronic format via EFS-Web and is hereby incorporated by reference into the specification in its entirety. The name of the text file containing the Sequence Listing is 6527_121805.ST25.txt. The size of the text file is 13,826 bytes, and the text file was created on Jun. 13, 2012.

Provided herein are methods of amplifying target nucleic acid sequences, kits for amplifying target nucleic acid sequences and reagents useful in those amplification methods.

Nucleic acid amplification is the backbone of many molecular biology and life sciences applications, including the rapidly growing area of molecular diagnostics. The method of polymerase chain reaction (PCR) is currently used as the method of choice of nucleic acid amplification. PCR however requires thermal cycling as it uses heat denaturation of double-stranded DNA products to promote the next round of DNA synthesis. Thus it is not very amenable to development of low cost and point of care molecular diagnostics. Hence there is a growing interest in the field of isothermal nucleic acid amplification and several such techniques have been lately reported over the past 2 decades, including nucleic acid sequence-based amplification (NASBA), self-sustained sequence replication (3SR); strand displacement amplification (SDA) ligase chain reaction (LCR), transcription mediated amplification (TCA) and loop-mediated isothermal amplification (LAMP). Each of these amplification methods have their own innovation as well as unique characteristics including advantages and disadvantages. For example, 3SR and NASBA eliminate heat denaturation by using a set of transcription and reverse transcription reactions to amplify the target sequence. Similarly, SDA eliminates the heat denaturation step in cycling DNA synthesis by employing a set of restriction enzyme digestions and strand displacement DNA synthesis with modified nucleotides as substrate. LAMP utilizes up to 6 primers with 8 separate binding sites to initiate production of several stem and loop structures. Despite the reports of several isothermal amplification methods, each method has some drawbacks. For example, NASBA and 3SR, are compromised in specificity, resulting mainly from the necessity to use a relatively low temperature of 40° C. for amplification. SDA largely overcomes these shortcomings by using four primers and isothermal conditions for amplification, but still has weak points: increased background due to digestion of irrelevant DNA contained in the sample and the necessity to use costly modified nucleotides as substrate. LAMP requires identification of 8 separate primer binding sites, making assay development a difficult process for some of the targets, such as RNA viruses that have a high rates of mutation in their replicative cycles.

SUMMARY

We have developed a novel isothemal DNA amplification method which is currently termed SPIDR (that is an acronym for SPiral Isothermal DNA Replication). This method has several variants and SPIDR1 utilizes a 4 primers (or more, e.g., two outer primers and two inner primers) arranged in a spiral manner, alternating between forward and reverse, across a length of DNA target. The primers are short (20-25 bases), linear and arranged in anti-parallel manner on the target DNA, cDNA and also RNA. The SPIDR2 method (second generation) utilizes, e.g., 5 primers, with two outer primers, e.g. of approximately 20-30 bases each and 3 inner primers of, e.g., 10-20 bases each with a 5' end portion that hybridizes to a first strand of a target nucleic acid sequence and a 3' end portion that hybridizes to a strand of the target sequence complementary to the first strand. A third generation SPIDR3 method utilizes a similar primer configuration as SPIDR1, with two outer primers and two inner primers, but adds two triplex spiral primers between the inner primers, each triplex spiral primer comprising 3' and 5' end portions that hybridize to a first strand of a target nucleic acid and a middle portion that hybridizes to a strand of the target sequence complementary to the first strand. The amplification methods utilize DNA polymerases with strand displacement activity and optionally exonuclease capabilities. The reactions proceed at an isothermal temperature ranging from 60-80 degrees and are thought to be exponential. It takes appx 30 to 60 minutes versus 90 to 120 minutes for a similar PCR reaction to accumulate $10^9$ or more copies with excellent sensitivity and specificity. When used with a DNA dye, e.g., an intercalation dye, the amplification products are visible to naked eye as a color change. The advantages of SPIDR over other isothermal techniques include the need for fewer primer binding sites, easier primer design, ability to use single enzyme reverse transcription and DNA polymerizations as well as a greater ability to detect targets that may have high rates of inherent genomic mutations, such as RNA viruses. The SPIDR1, SPIDR2 and SPIDR3 reactions may be multiplexed, for example with primers having different end-labels or tags such that the amplification products of each of the primer sets can be distinguished. An example of a method of distinguishing multiplexed amplification products is described below in the context of a lateral flow device.

BRIEF DESCRIPTION OF THE DRAWINGS

FIGS. 6A through 6H provide sequences showing the binding sites for the primers for SPIDR1 listed in Table 1 (SEQ ID NOs: 1-8, respectively).

FIG. 7 are photographs of gels showing a comparison of SPIDR1 (using Pyrophage) and LAMP (using Bst DNAP) I Amplification of several targets. Including (LAMP followed by SPIDR), *E. coli* and *Klebsiella pneumonae, Chlamydia, Staphylococcus aureus* and Dengue. NTC (or N): no target control. The amplification proceeds at an isothermal temperature ranging from 60° C.-80° C. and is thought to be exponential. It takes approximately 30-60 minutes versus 90-120 minutes for a similar PCR reaction. The amplification products are specific and visible as a smear or ladder on a gel.

FIG. 8 is a sequence showing the location of *E. coli* SPIDR2 primers of Table 2 on the genomic sequence (SEQ ID NO: 9). The outer primers (SPR-OF and SPR-O-R) are of approximately 20 bases while the inner primers are of approximately 10 bases. The inner primers consist of 5 sense and 5 antisense bases. The primer SPR I-F has the last 5 bases oriented in sense (forward) direction, while primer SPR I-R has the last 5 bases oriented in anti-sense (reverse) direction. The primer orientation is important for successful SPIDR amplification. The combination 1 works successfully for the SPIDR, while combination 2 (with reverse orientation of inner primers as compared to combination 1 primers) did not work in this assay.

FIG. 9 is a photograph of a gel showing successful SPIDR amplification of *E. coli* DNA is shown as a smear or ladder pattern. The orientation of inner primers appears to be important in this assay. The orientation as shown in Table 2 for the combination 1 set of primers was successful (Identified by #1) while combination 2 shown in Table 2 was not as successful (Identified by #2).

FIG. 10: SPIDR2 for Dengue virus showing strong fluorescence of a positive control on UV transillumination using Eva Green FIG. 11 provides a *Chlamydia* sequence (SEQ ID NO: 10) showing the binding sites for the SPIDR3 primers shown in Table 3.

DETAILED DESCRIPTION

Figure 1:
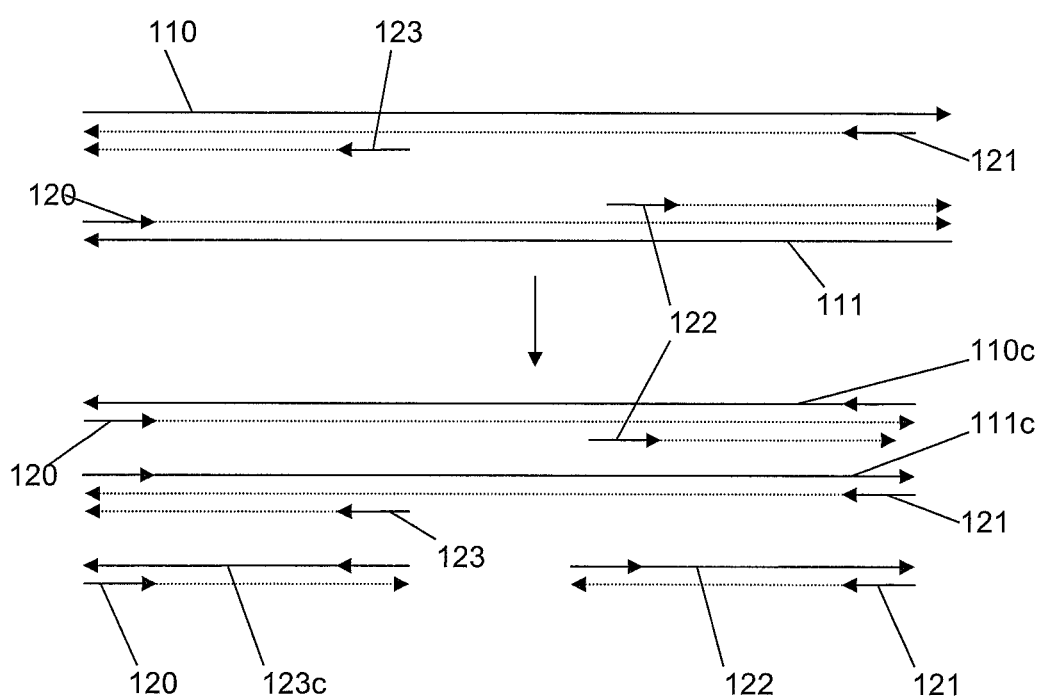
FIG. 1 is a diagram of a first non-limiting embodiment of the methods (SPIDR1) described herein, showing primer structure and orientation.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases. "Comprising" and like terms are open-ended. The terms "a" and "an" refer to one or more.

Provided herein are methods of amplifying target nucleic acid sequences, kits for amplifying target nucleic acid sequences and reagents useful in those amplification methods. The methods are preferably isothermal amplification methods. The methods utilize alternating primers that can be said to be oriented in a "spiral" configuration such that the nucleic acid products of the primers (amplicons) are typically longer than in typical two-primer PCR reactions with a single amplicon product. Because the method is isothermal, with primer sites being continually exposes, e.g. by strand displacement, and the length of the amplicon product increases over time, the rate of accumulation of specific product increases rapidly.

FIGS. 1-5 provide overviews of non-limiting embodiments of the methods described herein. In the methods described herein, as with PCR methods and other amplification methods, even though specific primers are used for each reaction, due to the nature of nucleic acids and polymerization reactions, the overall processes are sequence-independent; meaning a person of ordinary skill in the art can readily determine suitable specific primers for use in the methods based on the identification of a target sequence for amplification. This is seen with the multitude of PCR reactions and isothermal assays that have been developed, including the multiple specific reactions described in the Examples below. The SPIDR amplification methods are demonstrated herein to be effective. As such, one of ordinary skill in the art, based on the design constraints described herein, can develop a suitable SPIDR assay for most target sequences without undue experimentation. Primer design can be accomplished by visual inspection or by computer using any of the many publicly and commercially-available primer design computer programs, with primers typically ranging from 10 to 30 bases in length and typically devoid of significant secondary structure, such as hairpins. A primer is a single-stranded nucleic acid that hybridizes to another nucleic acid and from which a DNA sequence complementary to the nucleic acid to which the primer binds can be synthesized by elongation of the primer, e.g., from the 3' end of the primer by a 5'-3' DNA polymerase. As would be recognized by a person of ordinary skill, shorter, specific primers, for example, 5 or 6 bases in length can be utilized where a nucleic acid sample only has one instance, or a very limited number of instances, of the complement to the specific 5 or 6 base sequence. Alternately a particular sequence containing only one instance, or a very limited number of instances, of the specific 5 or 6 base sequence can also amplified with longer, more specific primers prior to or concurrently with amplification with the shorter primers, which bind the target sequence between the longer, more specific primers. In the methods described herein, a target sequence is amplified by longer, more specific, outer primers to increase the number of target sequences in a given reaction mix such that a typical 5-mer primer will predominantly amplify one sequence, or a limited number of sequences. The concept of complementarity of nucleic acids and the ability of wholly complementary or substantially complementary strands or nucleic acid to hybridize to each-other and/or to serve as DNA polymerase substrate is well-known to those of ordinary skill in the art. Tolerance of base-pair mismatches between primers and their complementary sequences, and that complementary strands are typically elongated with less than 100% fidelity are concepts that are well-known to those of ordinary skill and so long as the assays described herein proceed with substantial specificity and sensitivity and the described nucleic acid elements of the described reactions bind (hybridize) and function in the described intended manner, base pair mis-matches and less than 100% complementarity are tolerated and are within the scope of the described assays.

FIGS. 1-5 depict variations of the assays described herein. It should be recognized that FIGS. 1-5 are over-simplifications of the methods because the methods are typically conducted isothermally and therefore new sequences are often concurrently primed and elongated from displaced DNA strand as the displaced strands are being polymerized—resulting in a complex of nucleic acid, primers and polymerase enzyme, with multiple strands of DNA being elongated concurrently, that is too complex to represent in a drawing. In FIGS. 1-5, the 3' end of nucleic acid strands and the direction of elongation of the sequences by a 5' to 3' DNA polymerase are depicted by arrows.

In FIGS. 1-5, both strands are shown in order to show the arrangement of the primers on the respective strands, but as one of ordinary skill would recognize, only one of the first strand and the complementary strand is necessary for production of amplification products because primers are present that will produce a complementary strand. "Binding" of one nucleic acid sequence to another refers to sequence-specific hybridization of a sequence to its complementary sequence, as is known in the art, to form a nucleic acid duplex, e.g., double-stranded DNA (dsDNA). The initial template may be DNA or RNA, though if it is RNA, either the DNA polymerase used would have reverse transcription activity or a reverse transcriptase would be needed in the reaction mix to produce an initial DNA (cDNA) template for the amplification to proceed.

It will further be appreciated by those of ordinary skill in the art that any of the reactions described in FIGS. 1-5, and the Examples below, may be multiplexed, including both multiplexing of the same type of SPIDR reaction (e.g., two SPIDR1 reactions as further described in Example 5, below), or different types of SPIDR reactions (e.g., a SPIDR1 reaction combined with a SPIDR2 reaction). Any of the SPIDR reactions may be multiplexed with other types of isothermal assays.

FIG. 1 provides an overview of one embodiment of the methods described herein. First strand 110 and complementary strand 120 are depicted along with forward primer 120, reverse primer 121, internal forward primer 122 and internal reverse primer 123. Binding sites of the primers are shown and initial products of the primers are shown by dotted lines. The top diagram in FIG. 1 shows the initial binding sites of the primers 120, 121, 122 and 123 on strands 110 and 111 and possible elongation products are shown by dotted lines. The bottom diagram in FIG. 1 shows strands 110c, 111c, 122c and 123c produced by the reactions shown in the top diagram. Primers 120, 121, 122 and 123 are shown in the bottom of FIG. 1 binding to strands 110c, 111c, 122C and 123c. Using a strand displacing DNA polymerase with the described primer set surprisingly elongates isothermally without the need for initial and subsequent denaturation steps.

Figure 2:
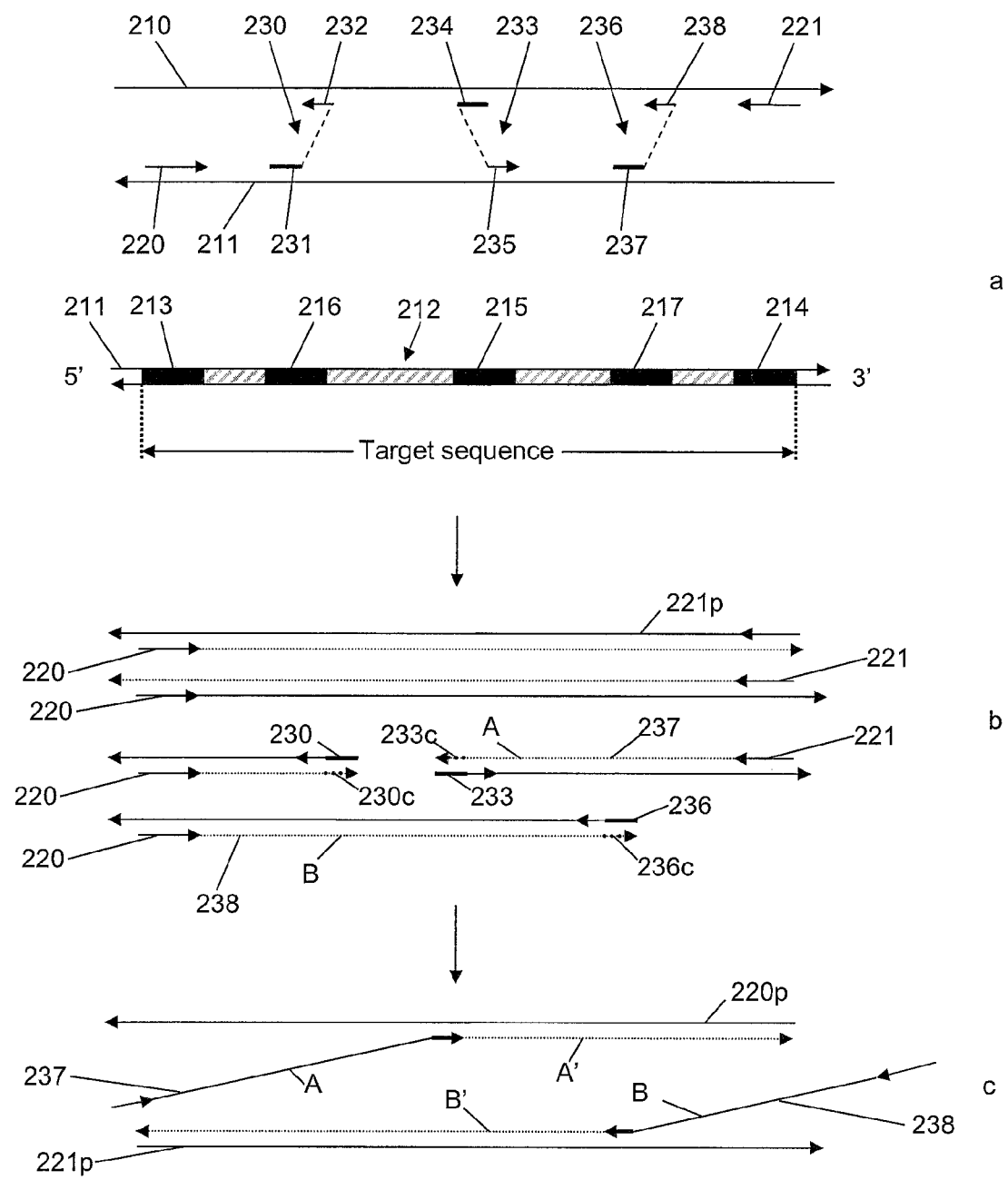
FIG. 2 is a diagram of a second non-limiting embodiment of the methods (SPIDR2) described herein, showing primer structure and orientation.

FIG. 2 provides an overview of one non-limiting embodiment of the sequence amplification methods described herein. In the figure, a (top) shows the arrangement of primers on the template strands. Depicted are a first strand 210 and complementary strand 211, which is complementary to the first strand. A duplex 212 of strands 210 and 211 is depicted aligned with the depiction of strands 210 and 211 and the primers within, showing target sequence (hatched) and first, second, third, fourth and fifth primer binding sites 213, 214, 215, 216 and 217, respectively within the target sequence. Orientation of duplex 212 is shown with the 5' end and the 3' ends depicted in relation to the directionality of the first strand 210.

Forward primer 220 and reverse primer 221 are depicted and together amplify the complete target sequence as in FIGS. 1A and 1B. The relative position of different primers in relation to strands 210 and 211 is in reference to the directionality of the first strand 210. Thus, primer 220 is 5' to primer 221, and conversely primer 221 is 3' to primer 220, even though primer 221 is depicted as binding at the 3' end of the target sequence on complementary strand 211.

Spiral primers 230, 233 and 236 each comprise a 5' portion and a 3' portion that each bind to different strands of the target sequence. Although one, two, three (shown), or more spiral primers can be used in this method, use of the spiral primers in combination with primers 220 and 221 permit production of additional elongation products, and produces product that can result in the formation of increasingly larger products over time. The overall effect of this is not only the production of more single-sized amplicons as with traditional PCR, but increasingly long amplification products with increasing numbers of primer binding sites, thereby producing amplification in an additional dimension as compared to traditional PCR products, with a more rapid accumulation of specific reaction product. The process has good fidelity due to the use of, for example, five primers, and does not use long or complex primers.

As shown in FIG. 2 a 5' end 231 of first spiral primer 230 is shown binding to complementary strand 211 and a 3' end 232 of the first spiral primer 230 is shown binding to the first strand 210. The first spiral primer 230 is said to be a reverse (R) primer because it primes elongation in a 3' to 5' direction in relation to the first strand 210. A 5' end 234 of second spiral primer 233 is shown binding to the first strand 210 and a 3' end 235 of the second spiral primer 233 is shown binding to the complementary strand 211. The second spiral primer 233 is said to be a forward (F) primer because it primes elongation in a 5' to 3' direction in relation to the first strand 210. A 5' end 237 of third spiral primer 236 is shown binding to complementary strand 211 and a 3' end 238 of the third spiral primer 236 is shown binding to the first strand 110. The third spiral primer 236 primes elongation in a reverse (R) direction. Thus the orientation of the three spiral primers 230, 233 and 236 located between the forward primer 220 and the reverse primer 221 is shown as R/F/R. 3' and 5' ends of spiral primers 230, 233 and 236 each are, independently, typically 5, 6, 7, 8, 9 or 10 bases in length. As shown in the Examples below, the 3' and 5' ends of spiral primers are 5 bases in length. Longer primers lead to more specificity, but are typically not necessary where the outer primers amplify a single sequence, e.g., in a typical human genomic DNA, mRNA or cDNA sample, and shorter primers may be preferred in many instances due to simplicity of design, less chance of secondary structure and other considerations, including cost.

In alternate embodiment to the method shown in FIG. 2, using the same outside primers and equivalent internal spiral primers, different internal primer orientations are possible, with essentially equivalent results expected, including F/R/F, FFR, RFF, RRR and FFF. Use of more than three or less than three internal spiral primers configured as depicted in FIG. 2, also is expected to function essentially equivalently, for example: with one internal spiral primer, F or R; with two internal spiral primers FF, FR, RF and RR; and with four or more internal primers, all permutations of F and R primers are expected to yield equivalent results, though the complexity of the reaction increases with each primer added.

FIG. 1 b (middle) shows the initial reaction products of a reaction performed with both strands 210 and 211 in the reaction mix and the five primers depicted in FIG. 1 a. Reaction product extending from primer 220 is designated 220p and reaction product extending from primer 221 is designated 221p, with the primers shown integrated into the products 220p and 221p. Primers 220 and 221 are shown bound to products 220p and 221p, with the extension products that are produced therefrom shown by dashed lines. Likewise, the reaction products extending from the 3' ends of the depicted internal spiral primers 230, 233 and 236 are depicted (solid lines), with the primers integrated into the product. Primers 220 and 221 are shown bound to the reaction products extending from the spiral primers, with the reaction products extending from those primers shown by dotted lines. As can be seen, the reaction products produced from the products of the spiral primers now have 3' end sequences 230c, 233c and 236c that are complementary to the sequences of the spiral primers, which can then be used as primers to produce further reaction products. The target sequence portions A and B produced by extension of primers 221 and 220, respectively to produce reaction products 237 and 238, respectively, are shown in FIG. 1 b.

FIG. 1 c (bottom) depicts two among many possible reaction products of the reactions shown in FIG. 1 b to illustrate extension of the amplification products beyond the size of the initial template. The interaction between reaction product 220p and the reaction product 237 containing 3' end sequence 233c and target sequence portion A is shown. The elongation product is shown, which contains a repeat A' of target sequence A. Also shown is the interaction between reaction product 221p and the reaction product 238 containing 3' end sequence 236c, complementary to internal spiral primer 236, and target sequence portion B is shown. The elongation product is shown, which contains a repeat B' of target sequence B.

Portion A comprises the binding sites 214 and 217 and portion B comprises the binding sites 213, 215 and 216, such that as the reaction proceeds, primers bind to single-stranded portions of the reaction products such that an amplification cascade proceeds as additional binding sites are exposed. Facilitating this process is the continuous strand displacement of a DNA polymerase with strand-displacement activity, as described herein. In theory, similar reactions can occur using standard PCR cycling (that is denaturing between cycles) and using a non-strand-displacing polymerase, but the reaction would not occur with the same continuous cascade of primings and elongations that would occur in an isothermal reaction with a strand-displacing DNA polymerase. As indicated above, the orientation of the spiral primers, depicted in FIG. 1 a as R/F/R can be reversed to a F/R/F orientation, or other orientations with similar results expected.

Figure 3A:
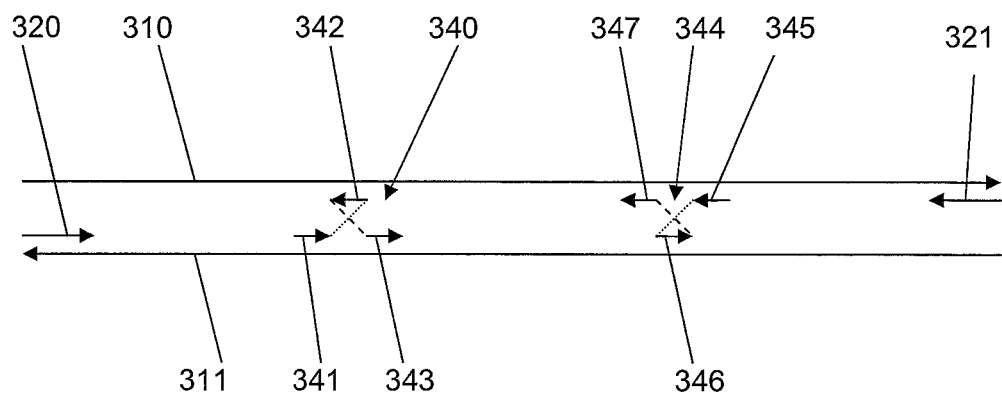
FIGS. 3A and 3B are diagrams of a third and fourth non-limiting embodiment of the methods described herein, showing primer structure and orientation.

FIG. 3A depicts a third primer configuration. In FIG. 3A, first strand 310, complementary strand 311, outside forward primer 320 and outside reverse primer 321 are depicted. Internal triplet spiral primers 340 and 344 are depicted. Each of internal spiral primers 340 and 344 comprise three parts. 5' ends 341 and 345, middle portions 342 and 346 and 3' ends 343 and 347 of primers 340 and 344 are shown. The 5' and 3' ends 341, 343, 345 and 347 of each the internal triplet spiral primers 340 and 344 are in the same orientation, while their middle portions 342 and 346, respectively are in the opposite orientation such that the middle portions 342 and 346 of each the internal triplet spiral primers 340 and 344 bind the opposite strand that the 5' and 3' ends 341, 343, 345 and 347 bind. The internal triplet spiral primers 340 and 344 are oriented in either a forward (primer 340) or reverse (primer 344) direction, indicative of the direction the primer elongates with respect to the first strand 310. Depicted in FIG. 3A is a FR orientation.

Figure 3B:
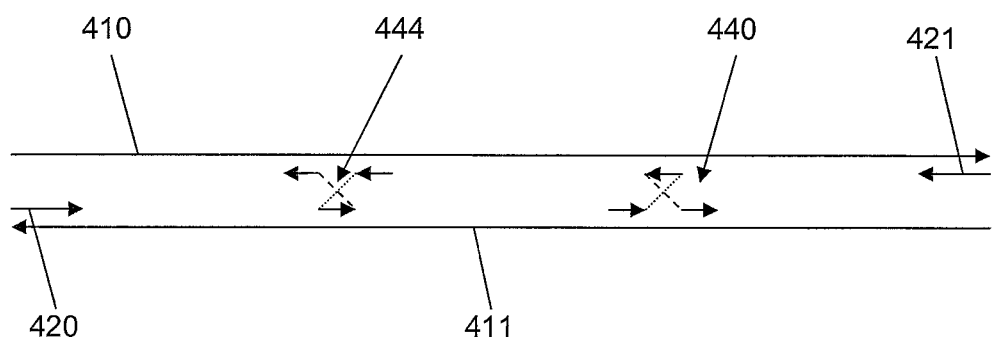

FIG. 3B provides an alternate embodiment of the method shown in FIG. 3A. First strand 410 and complementary strand 411 are shown, and primers 420 and 421 are in the same orientation as in FIG. 3A. The binding site of the internal primers 440 and 444 are reversed in the RF orientation, with expected similar results to the FR orientation of FIG. 3A. Use of additional internal triplet spiral primers, for example 3, 4 or 5 internal triplet spiral primers, is expected to yield equivalent results.

Figure 4A:
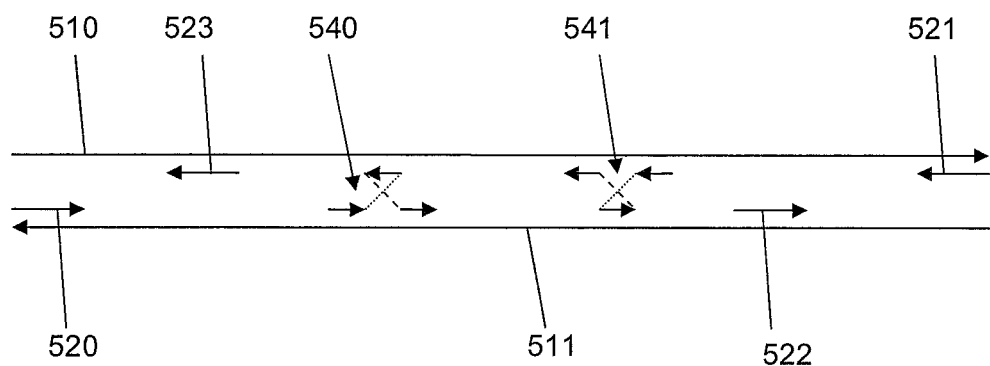
FIGS. 4A and 4B are diagrams of a fifth and sixth non-limiting embodiment of the methods described herein, showing primer structure and orientation.
Figure 4B:
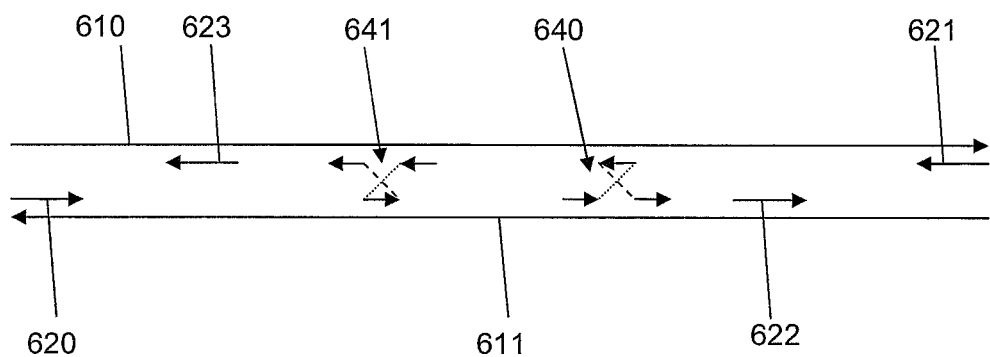

In further embodiments, methods are provided using combinations of the internal primers depicted in FIGS. 1-3. FIG. 4A provides a combination of the primer configuration depicted in FIG. 1 with two internal triplet spiral primers as shown in FIG. 3A. First strand 510 and complementary strand 511 are shown, and primers 520, 521, 522 and 523 are in the same orientation as in FIG. 1. Internal triplet spiral primers 540 and 541 are provided in the F/R configuration as in FIG. 3A. FIG. 4B provides a combination of the primer configuration depicted in FIG. 1 with two internal triplet spiral primers as shown in FIG. 3B. First strand 610 and complementary strand 511 are shown, and primers 620, 621, 622 and 623 are in the same orientation as in FIG. 1. Internal triplet spiral primers 640 and 641 are provided in the R/F configuration as in FIG. 3B.

Figure 5A:
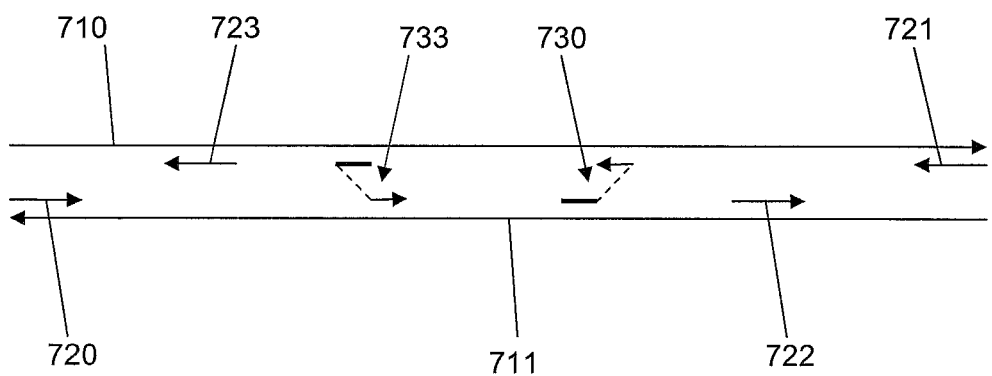
FIGS. 5A and 5B are diagrams of a seventh and eighth non-limiting embodiment of the methods described herein, showing primer structure and orientation.
Figure 5B:
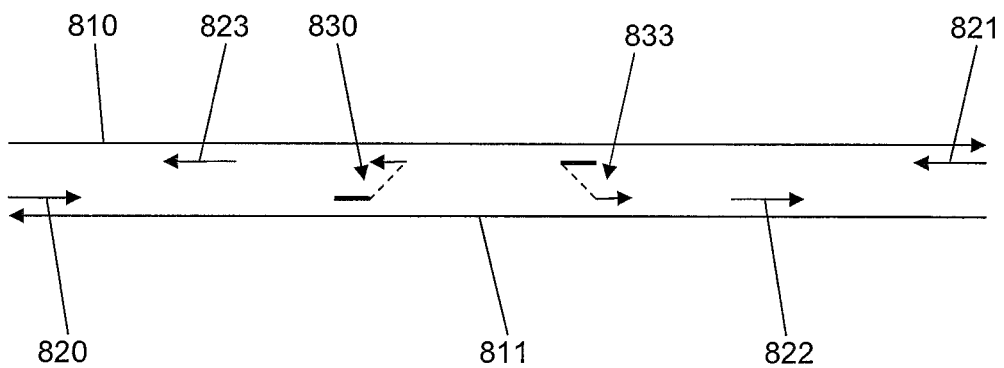

FIG. 5A provides a combination of the primer configuration depicted in FIG. 1 with two spiral primers as shown in FIG. 2. First strand 710 and complementary strand 711 are shown, and primers 720, 721, 722 and 723 are in the same orientation as in FIG. 1. Internal spiral primers 730 and 733 are provided in an F/R configuration. FIG. 5B provides a combination of the primer configuration depicted in FIG. 1 with two spiral primers as shown in FIG. 2 in opposite orientation as the primers of FIG. 5A. First strand 810 and complementary strand 811 are shown, and primers 820, 821, 822 and 823 are in the same orientation as in FIG. 1. Internal spiral primers 830 and 833 are provided in an R/F configuration.

In addition to the embodiments depicted in FIGS. 4A, 4B, 5A and 5B, additional combinations of the primers of FIG. 1 and one or both of the forward and/or reverse Internal spiral or triplet spiral primers depicted in FIGS. 4A, 4B, 5A and 5B may be used.

In each embodiment depicted in FIG. 1-5, a DNA polymerase with strand displacement activity and optionally reverse transcriptase activity can be utilized. Further, in any embodiment of the assay described herein, and reagents and kits for use in implementing those methods, one or more of the primers may be attached to (labeled with) a tag, such as a dye, an enzyme, a ligand, an epitope, an antigen etc. facilitating specific detection of reaction products by any useful method, many of which are known to those of ordinary skill in the art for detecting macromolecules. An example of a useful method is described below in the context of the lateral flow device. Non-limiting examples of such tags include biotin, avidin/streptavidin, fluorescent dyes, compounds to which antibodies are raised, such as FITC, etc.

As used herein, "isothermally amplified" or "isothermal amplification" and like terms refers to a method of amplifying nucleic acid that is conducted without a denaturation step unlike traditional PCR reactions. This requires that the DNA polymerase is a DNA polymerase having strand displacement activity. Isothermal amplifications are often conducted at substantially a single temperature because primers bind to displaced DNA strands. In isothermal amplifications the reaction mixture comprising the nucleic acid sample and optionally all primers may be heated to a denaturation temperature at which double-stranded nucleic acid in the reaction mixture denatures into single strands (e.g., at least 85° C.-90° C.) prior to the amplification and optionally prior to addition of the DNA polymerase when the DNA polymerase is inactivated at the denaturation temperature. In one example of an isothermal amplification or non-isothermal amplification (having a denaturation step between cycles), the reaction mixture is first amplified at an annealing and elongation temperature that permits production of a first amplification product from longer outer primer sets and then the annealing and elongation temperature is lowered so that the spiral primers can bind to the template.

As used herein, a DNA polymerase with strand displacement activity is a 5' to 3' DNA polymerase enzyme that catalyzes the strand displacement-type reaction for synthesis of a complementary chain. Use of a DNA polymerase with strand displacement activity facilitates the use of an isothermal reaction because the nucleic acid product does not need to be denatured after every cycle. The DNA polymerase with strand displacement optionally includes 3' to 5' exonuclease activity. A primer is annealed to a nucleic acid template, and the primer is extended by the polymerase at a desired reaction temperature that minimizes non-specific hybridization of nucleic acids in the reaction mixture, yet is not too high to prevent specific annealing of primers in the reaction mixture and thermal deactivation of the polymerase. Because each primer for each given sequence typically has a different melting temperature (Tm) due to its unique sequence and the composition of the particular reaction mixture and each polymerase typically has a specific optimal polymerization temperature and inactivation temperature, each reaction is optimized in terms of reaction temperature by (e.g.) conducting the same reaction at different temperatures. Certain DNA polymerases may be preferred due to their stability at higher reaction temperatures, for instance, between 60° C. and 85° C. For instance Bst Polymerase is active to about 70° C. and Pyrophage 3172 (Lucigen, Middleton, Wis., see also U.S. Pat. No. 8,093,030) is active over 80° C. Optimization of any give reaction can easily be accomplished by a person of ordinary skill in the art. The DNA polymerase with strand displacement activity may include the ability to reverse transcribe RNA, for instance by lacking 3'-5' proofreading function, as with Pyrophage 3172—permitting one-tube reverse transcription and amplification reactions. The DNA polymerase with strand displacement activity preferably lacks exonuclease and endonuclease activity, such as nicking and 5'-3' nick translation activity.

Non-limiting examples of DNA polymerase with strand displacement activity include: Bst DNA polymerase; Bst DNA polymerase large fragment; Bca (exo-)DNA polymerase; DNA polymerase I Klenow fragment; Bsu DNA Polymerase, large Fragment (New England Biolabs); Vent DNA polymerase; Vent (exo-)DNA polymerase (Vent DNA polymerase deficient in exonuclease activity); Deep Vent DNA polymerase; Deep Vent(exo-)DNA polymerase (Deep Vent DNA polymerase deficient in exonuclease activity); φ29 phage DNA polymerase; MS-2 phage DNA polymerase; and TopoTaq DNA Polymerase (Fidelity Systems, Inc. Gaithersburg, Md.).

The reactions described herein are typically carried out isothermally, that is at one temperature at which specific priming, polymerization and strand displacement occurs. In a preferred embodiment, but because of the adjustment of melting temperature (Tm) etc., it is not always possible to utilize temperature conditions desired for the stability of the enzyme. Accordingly, it is one of the desired conditions that the enzyme is thermostable. Although the isothermal reaction described herein surprisingly progresses without an initial denaturation step, heat denaturation may be conducted to provide nucleic acid as a first template, and in this respect too, utilization of a thermostable enzyme broadens selection of assay protocol. Further, utilization of a single strand binding protein often promotes the synthesis of a complementary chain. One non-limiting example of a single-strand binding protein is T4 gene 32 (New England Biolabs). Other additive co-factors, reagents, proteins, enzymes such as recombinases, may be utilized to optimize the reactions described herein.

As described herein, a reaction mixture is a mixture of reagents in which the amplification reactions described herein are supported. Reaction mixtures typically comprise primers, a nucleic acid sample optionally comprising a target sequence, buffers (e.g., TRIS-HCl), chelating agents, salts and/or ions (e.g., KCl, $(NH_4)_2SO_4$, a betaine and $MgSO_4$), a detergent (e.g., a nonionic detergent such as Triton X-100), deoxyribonucleotides (dNTP), and any other ingredient that are useful in supporting and/ore optimizing a particular reaction, such as a dye for detection of duplexed nucleic acid accumulation, a probe for detection of product, single strand binding proteins or recombinase enzymes, reverse transcriptase. Useful and optimal concentrations of each ingredient can be determined empirically. The reaction mixture is incubated at a temperature or combination of temperatures effective to produce amplification products using any given assay. Optimal temperature ranges and patterns are determined empirically.

The reaction products can be detected by any method for determining accumulation of duplexed nucleic acid, or specific nucleic acids. As described herein, the accumulation of specific amplification product can be determined by visualization on a gel as shown in the Examples, by visual or spectrophotometric intercalation of a dye as shown in the Examples, by specific binding to a probe, by use of tagged primers so that detection of amplification product is detected visually (as with the device of FIGS. 13A and 13B), or by any of the many ways known by those of ordinary skill in the art for detection of accumulation of either duplexed DNA or specific nucleic acid sequences.

Figure 13A:
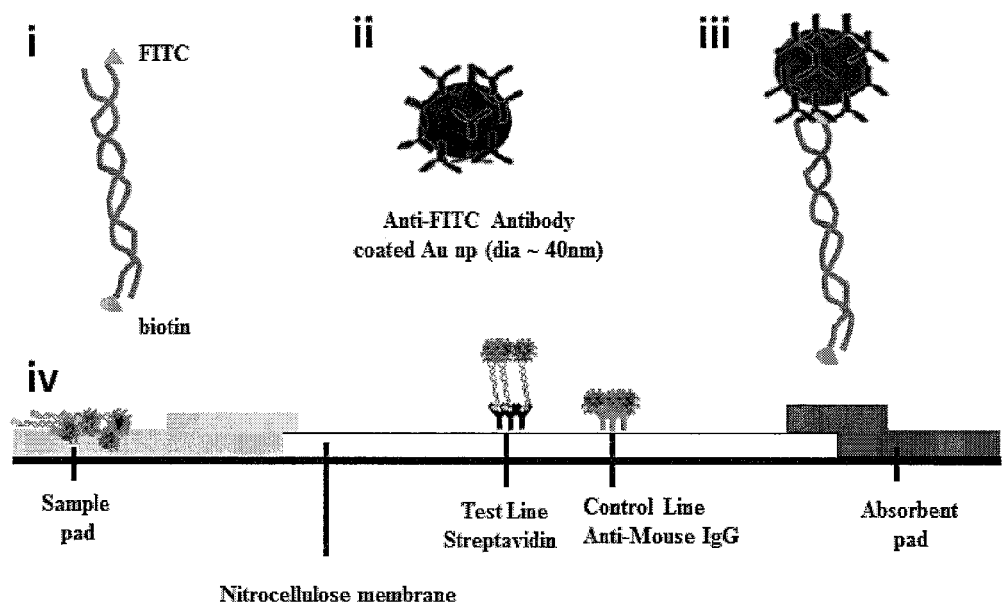
FIGS. 13A and 13B depict schematically a lateral flow device useful for detection of the amplification products produced by the methods described herein.
Figure 13B:
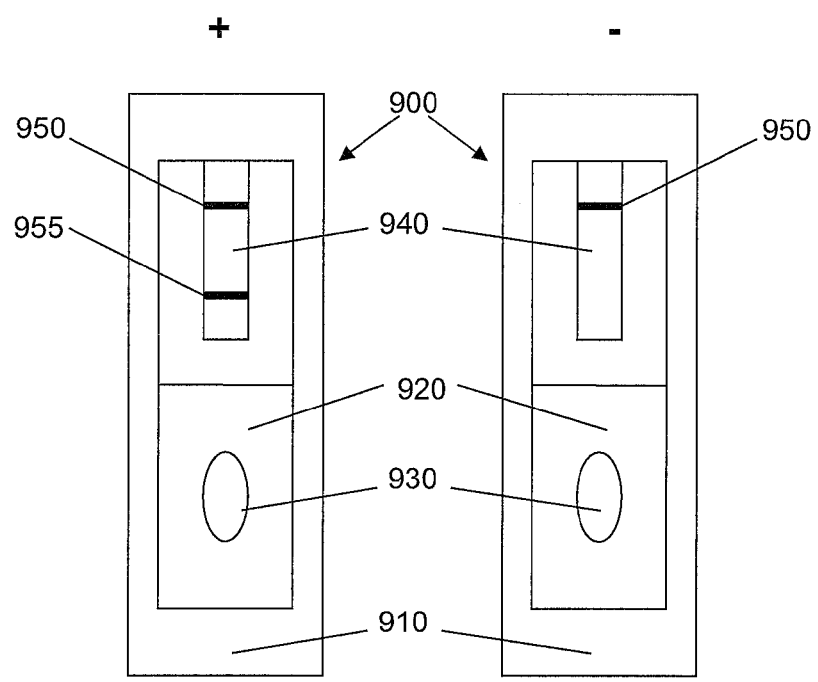

FIGS. 13A and 13B depict schematically one embodiment of a lateral flow device useful in the detection methods described herein. In reference to FIG. 13A, one of the primers used for amplification is end-labeled at their 5' ends with a first tag, such as FITC (fluoresceine isothiocyanate), and a second primer that produces a product complementary to the product of the first primer is labeled with another tag, such as biotin. Any reaction products produced by the two primers will produce duplexed DNA that is dually labeled at opposite ends with the two tags, as indicated in FIG. 13A(i). In the figure, gold particle-conjugated antibodies directed to the first tag (FITC in this example) are deposited in the path of the sample on the membrane adjacent to the sample pad, binding FITC in the sample. If there is a reaction product, the first-tag-bound nucleic acid will be bound to a complementary strand with the second tag. A substrate, such as nitrocellulose, is provided that has a ligand for the second tag (streptavidin is depicted) printed or otherwise patterned thereon, as well as a ligand that binds the gold particle-conjugated antibodies as a positive control, such as anti-mouse IgG which in the depicted example binds the anti- FITC mouse IgG antibody bound to the gold particles. If there is reaction product that contains dually-labeled duplexed DNA, the DNA/gold particles will bind to the site containing the ligand for the second tag. Whether or not there is dually-labeled duplexed DNA, the gold particles will bind to the ligand that binds to the gold-particle-conjugated antibodies. Detection of the bound particles may be performed either visually, or by otherwise detecting the particles, such as by a color-change reaction by linking the particles with an enzyme such as horseradish peroxidase, by fluorescence of the tag, or otherwise. As one of ordinary skill in the art, the choice of the first tag and the second tag, as well as the ligands that bind those tags, alternatives for gold particles, and the method by which binding events are detected may vary greatly and a person of ordinary skill would be able to identify useful combinations. As is shown in the embodiment depicted in FIG. 13A, sample is placed on a sample pad or similar structure, passed through and/or about a nitrocellulose membrane onto which ligands for the second tag and the gold particle are printed or otherwise patterned, and the sample ultimately is absorbed into an absorbent pad in order to wick or otherwise draw the sample from the sample pad past the membrane-bound ligands, and to the absorbent pad.

FIG. 13B shows a lateral flow device showing positive and negative results. Device 900 comprises a backing 910, a sample pad cover 920 covering the sample pad depicted in FIG. 13A, an opening 930 in the sample pad cover 920 into which sample is deposited, and nitrocellulose membrane 940 onto which the ligand for binding the second tag (e.g. streptavidin when the second tag is biotin) and the ligand for binding the gold particle are patterned in two lines. In the device 900, the gold particles are deposited on either the sample pad beneath the cover 920 or on the membrane 940 between the opening 930 and the binding site for the second tag (corresponding to line 955). Patterning the ligands into lines is not necessary and is done solely for the purpose of illustration, as any useful pattern, such as dots, circles, letters, etc. would be equally useful. In both the positive (left) and negative (right) results depicted, binding of the gold particles to their ligand is shown as a line 950. Binding of the second tag to its ligand is shown as a line 955 in the positive sample, but not in the negative sample. Variations in the method, detection reagents and device structure, including the pattern of the ligands on the membrane, are a matter of ordinary design choice.

In a variation of the method illustrated in FIGS. 13A and 13B, a third line, or even more lines (or other patterns), of a different antibody or ligand can be patterned onto the membrane such that in the case of a multiplexed SPIDR reaction, the reaction products of two or more SPIDR reactions can be distinguished. As shown in Example 5, below, two different SPIDR reactions were multiplexed, with one inner primer of reactions products being biotin-labeled, and other inner primers of the first multiplexed reaction (*E. coli*) being labeled with FITC and of the second multiplexed reaction (*K. pneumoniae*, or "*Klebsiella*") being labeled with digoxigenin. The membrane of the lateral flow device has discrete locations patterned with anti-FITC antibody, anti-digoxigenin antibody and anti-biotin antibody, as *E. coli* positive, *Klebsiella* positive and positive control sites on the membrane, respectively. In the depicted assay, the gold particles are labeled with streptavidin. The positive control site binds biotin which in turn binds the streptavidin of the gold particles.

In the methods described herein useful reagents include the various primer types described in connection with FIGS. 1-5 and the Examples below. Examples of primers include the single-sense (first strand hybridizing or complementary strand hybridizing, e.g., sense or antisense) outer or inner probes described in connection with FIG. 1, the internal spiral probes having 5' portion of one strand orientation and a 3' end of opposite strand orientation, and internal triplex spiral primers having a 3' and 5' portion of one strand orientation and a middle portion of opposite strand orientation. As would be understood by those of ordinary skill in the art, the reagents described herein are equally applicable to may different target sequences and a person of ordinary skill can determine suitable primers based on the descriptions of the primers provided herein without undue experimentation.

Reagents also include other ingredients that are used in any reaction mixture described herein. Kits are packaged combinations of reagents that are useful commercializing and facilitating use of the methods. Platform-specific cartridges containing reagents useful in the described reactions and reaction mixtures are considered to be kits. A kit comprises packaging plus one or more useful reagents. Indicia providing instructions as to how to perform a given reaction using the reagents of a kit also may be provided in the kit. At a minimum, a kit comprises one or more primers useful in any of the reactions described herein, for example any of the primers depicted in Tables 1, 2 and 3, or combinations of those primers. A reagent kit may comprise the four primers shown in FIG. 1, the five primers shown in FIG. 2, or the six primers shown in FIG. 4A or 4B. A reagent kit also optionally comprising additional reagents useful in performing the reaction, including buffers, polymerase enzymes, dNTPs, salts, etc. A positive control DNA or RNA sample may be included in the kit. A kit may include some or all of the reagents described above in connection with the lateral-flow detection device and method shown in FIGS. 13A and 13B, or variations thereof, including a device as depicted in FIG. 13B.

The following Examples are provided as non-limiting illustrations of the various SPIDR methods and reagents described herein.

Example 1

SPIDR1 Reaction

Variations on the SPIDR reactions are essentially described in FIGS. 1-5. The following description of the example pertains to SPIDR1, but several aspects of assay setup, master mix composition and detection methods are similar for the different SPIDR variants described herein.

A typical SPIDR reaction is carried out in a total 20 µl reaction mixture containing 0.8 µM each FIP and BIP, 0.2 µM each F3 and B3, 400 µM each dNTP, 1 M betaine (Sigma), 20 mM Tris-HCl (pH 8.8), 10 mM KCl, 10 mM (NH4)2SO4, 4 mM MgSO4, 0.1% Triton X-100 8 U Bst DNA polymerase large fragment (New England Biolabs) or 30 Units of Prophage enzyme (LUCIGEN) and the specified amounts of double-stranded target DNA. The mixture is incubated at different temperatures of 60-85° C. for 30-90 minutes, then reaction products are visualized by a variety of methods.

Design of SPIDR1 Primers: The SPIDR primers were designed by visual inspection of target genomic sequences and checked by the software Primer3 (for various characteristics such as: Tm, self-complementarity, etc).

SPIDR1 Primers for reactions as depicted in FIG. 6 are shown in Table 1.

TABLE 1

SPIDR1 PRIMERS

| Organism | Primer | Sequence | SEQ ID NO: |
|---|---|---|---|
| Influenza A M1 Region | OUTER-F | 5'-GAGTCTTCTAACC GAGGTCGAAACG-3' | 11 |
|  | OUTER-R | 5'-TTCCCATTGAGGGC ATTTTGGAC-3' | 12 |
|  | Inner-R | 5'-GTTCTTTCCAGCAA AGACATC-3' | 13 |
|  | Inner F | 5'-GTGTTCACGCTCAC CG-3' | 14 |
| Influenza B M1 Region | OUTER-F | 5'-TATGTCGCTGTTTG GAGACAC-3' | 15 |
|  | OUTER-R | 5'-GAGCGTTCCTAGTT TTACTTGC-3' | 16 |
|  | Inner-R | 5'-CCAAGGCAGAGTCT GGTC-3' | 17 |
|  | Inner F | 5'-GAAATAGCAGAAGG CCATG-3' | 18 |
| West Nile | OUTER-F | 5'-GGGATTGACACCAAT GCATAC-3' | 19 |
|  | OUTER-R | 5'-CCATCTTCACTCTAC ACTTC-3' | 20 |
|  | Inner-R | 5'-AGCACTGCTCCAAGG GAGG-3' | 21 |
|  | Inner F | 5'-GCATCAAGCTTTGGC TGGAGC-3' | 22 |
| HIV B/C | OUTER-F | 5'-RAAGGCTTTYAGCC CAGAAR-3' | 23 |
|  | OUTER-R | 5'-TCTCCYACTGGGRAYA GGTGG-3' | 24 |
|  | Inner-R | 5'-TAAATCTTGTGGGG TGGCTC-3' | 25 |
|  | Inner F | 5'-CATAGCAGGAACTAC TAGTACCCTT-3' | 26 |
| DENGUE | OUTER-F | 5'-CWGGCCTGTAGCT CCRYC-3' | 27 |
|  | OUTER-R | 5'-GAACCTGTTGRWT CAACARCACC-3' | 28 |
|  | Inner-R | 5'-GGGAGGGGTCTCC TCTAACC-3' | 29 |
|  | Inner F | 5'-AGACCAGAGATCC TGCTGTCTC-3' | 30 |
| E COLI | OUTER-F | 5'-GCCGCGTTCTCA TCCTCCCG-3' | 31 |
|  | OUTER-R | 5'-CTGGTGATCGTC TCAAGCCCGGC-3' | 32 |
|  | Inner-R | 5'-CATTTTGCAGCT GTACGC-3' | 33 |
|  | Inner F | 5'-CTGGGGCGAGGT CGTGGTAT-3' | 34 |
| KLEBSIELLA | OUTER-F | 5'-AAACTGATTGG TCTGCCGG-3' | 35 |
|  | OUTER-R | 5'-GACGATCACCA GCAGGTTG-3' | 36 |
|  | Inner-R | 5'-GCAGACGCGG AGACAC-3' | 37 |
|  | Inner F | 5'-CTTCCGCACC GCGGTC-3' | 38 |
| CHLAMYDIA | OUTER-F | 5'-CATCGGTCAAC GAAGAGGTT-3' | 39 |
|  | OUTER-R | 5'-CATCTTTGCGG' TTGCGTGTCC-3' | 40 |
|  | Inner-R | 5'-GCCTTAACC CCACCA-3' | 41 |
|  | Inner F | 5'-ATAACCCCGCA CGTGCTTCG-3' | 42 |

Analysis of Amplification Products:

Aliquots of 5 µl of SPIDR products were electrophoresed in 2% agarose gels (0.5×TBE) followed by staining with SYBR Green I (Molecular Probes Inc.). They were also visualized by naked eye inspection addition of various DNA binding dyes to the reaction product mix after the completion of reaction. The dyes included SYBR green I dye, Eva Green dye and GR Safe dye at different concentrations. One microliter of SYBR green I dye (1:100 dilution of a 10,000× stock solution) was added to tubes containing SPIDR products. We also used other nucleic acid stain dye, ie GR safe and Eva green dye for visual detection of SPIDR products using pre-diluted concentrations provided by the manufacturer.

Bst Pol is the standard enzyme used for several isothermal reaction protocols such as LAMP. Although its characteristics are favorable for LAMP, we have evaluated other enzymes with broader applications. Some of these are described below.

There are several requirements of an enzyme used in isothermal amplification. Strand displacement is obligatory to allow the reaction to cycle isothermally. At least moderate thermostability appears to be necessary to allow partial heat denaturation. A 3'-5' exonuclease activity is important to remove single base extensions that will interfere with priming in the next round of amplification. Currently the reaction temperature for isothermal assays is constrained to under 60-65° C. by the moderate thermostability of Bst Pol, which limits efficiency and specificity of primer binding. In preliminary studies, analysis of samples with high protein content like stool, blood etc. required heating the samples to 85° C. prior to isothermal amplification. This requires a two-step process of preheating the sample, followed by addition of enzyme for amplification, which introduces an opportunity for operator error and interferes with streamlining of the process Using the primers of Table 1, we compared the ability of Lucigen's new DNA Pol enzymes (Pyrophage 3173 shown in FIG. 7) with Bst DNA pol for ability to catalyze SPIDR reactions and also tested its higher thermostability. Our preliminary data using various amplification protocols described herein (SPIDR1-3) shows that the enzyme can be also useful at high temperature isothermal reactions. Pyrophage 3173 performed well at 82° C. and was almost as robust as Bst DNA pol catalyzed reactions at 65° C. Bst DNA Pol did not work at 82° C. (data not shown). We have now used SPIDR and LAMP to compare the amplification of genomes of several DNA and RNA infectious agents, such as *E. coli, Klebsiella, Chlamydia, Staphylococcus aureus* and RNA viruses like Dengue, Influenza, and HIV. One additional advantage of Pyrophage is that it has inherent reverse transcriptase activity, thus precluding the need for a separate RT enzyme and step (as needed for LAMP for RNA viruses). Results of some of these preliminary studies demonstrated comparable amplification efficiency and limits of detection for both protocols and are shown in FIG. 7

Example 2

Amplification of Cloned *E. coli* DNA and Other Targets Using SPIDR2

An *E. coli* sequence was detected using the SPIDR2 amplification method depicted in FIG. 2. The SPIDR2 method depicted in FIG. 2 relies on auto-cycling strand displacement DNA synthesis that is performed by a DNA polymerase with high strand displacement activity and a set of inner and outer primers. In the initial steps of the SPIDR reaction, the outer primers (SPR-O-F and R) are used, but later during the cycling reaction all the primers (Outer and Inner primers (SPR1, 2 and 3) are used for strand displacement DNA synthesis. The inner primers are called the SPIRAL Inner Forward primer (SPR-I-F) and the SPIRAL Inner Reverse primer (SPR-I-R) and are labeled 1, 2 or 3 depending upon the position in the genomic target. Each SPIRAL Inner primer is of approximately 10 bases each and contains two distinct sequences corresponding to the sense and antisense sequences of the target DNA, one for priming in the first stage and the other for self-priming in later stages. For ease of explanation, the sequences (typically 10 nt) inside both ends of the target region for amplification in a DNA are designated antisense or sense (that is, A or S). As an example SPR IF1 consists of 5 antisense (A) and 5 sense (S) bases, respectively (Table 2) and the SPR-I-R consists of 5 sense (S) and 5 antisense (A) bases. Given this structure, the sequences of SPR-I-F and SPR-I-R were designed as follows (5A+5S bases and 5S+5A bases). The two outer primers consist of SPR-O-F and the SPR-O-R sequences (SPR-O-R is complementary to target DNA sequence) and are approximately 20-23 bases long. A DNA sample containing the target sequence and the 5 primers is mixed with the SPIDR reaction components is then initiated by addition of respective enzymes and carried out at 60-65° C. for up to 1 h in the case of the Bst DNA polymerase or 60-80° C. for up to 1 h for Pyrophage.

Without any intent of being bound by this theory, in a reaction using a primer configuration of this example, the outer and inner primers hybridizes to the target DNA and initiates complementary strand synthesis. Outer primers initiate the longest sequence polymerization. The inner primers initiate strand displacement DNA synthesis, releasing an inner primer-linked complementary strand, which can form a spiral structure at one end. This single-stranded DNA serves as template for outer as well as inner primer-initiated DNA synthesis and inner primer-primed strand displacement DNA synthesis, leading to the production of multiple spiral DNA structures (SPIDRS) connected to backbone of various lengths. These SPIDRS of various backbone lengths then serve as the starting material for further SPIDR cycling, in the second and subsequent stages of the SPIDR reaction. The final products are a mixture of Spiral DNA branches with various back bone lengths formed by annealing between alternately inverted repeats of the target sequence in the same strand. The use of 5 primers (recognition of 5 distinct sequences) in the initial and the subsequent steps ensures high specificity for target amplification. Therefore, target selectivity is expected to be higher than those obtained in PCR and SDA.

In order to further demonstrate the mechanism, the efficiency, the specificity and the ease of use of SPIDR, we chose *E. coli* DNA as a model target DNA and prepared 5 primers that met the SPIDR2 requirements. The reaction was carried out at 65° C. for 1 h and the products were separated by agarose gel electrophoresis and also identified by naked eye visualization. The SPIDR reaction produced many bands of different sizes from ~200 bp to the loading well. Production of the bands depended on the presence of the primers, the template and DNA polymerase.

We generated and quantified a plasmid containing the target *E. coli* sequence (pECOLIT3). Briefly, a 207-bp target DNA sequence spanning the *E. coli* genome was amplified by PCR using the same outer primers as those used in the SPIDR reaction (i.e., 0.2 µM each SPIDR-F and SPIDR-R primers). The amplified product was then cloned into a TOPO cloning vector, using a TA cloning kit according to the manufacturer's instructions (Invitrogen, CA). The vector was used to transform XL1-Blue competent *E. coli* cells (Stratagene, CA). The transformed cells were incubated overnight and the colonies with the insert (using blue-white distinction) further grown. The cloned insert was isolated from the cells by use of a Fast Plasmid mini kit (Eppendorf, NY). The presence of the positive clone was tested by digestion of the plasmid DNA by EcoRI, followed by gel electrophoresis and sequencing. The pECOLIT3 clone was quantitated using UV spectrophotometry at 260 nm (SmartSpec 3000; Bio-Rad Laboratories, CA). A series of 10× dilutions, spanning 10 to $10^7$ copies/tube of the clone, was used to test the sensitivity of the SPIDR reactions. The SPIDR reaction was carried out at 65° C. for 45 min. Aliquots of 2 µl of the amplification products were mixed with 300 µl of 1/10 000 diluted original SYBR Green I in 10 mM Tris-HCl (pH 8.0), and 1 mM EDTA, incubated at room temperature for 30 min and quantified for fluorescent intensity with the SmartSpec 3000 spectrophotometer. Primers are shown in Table 2, and in FIG. 8.

TABLE 2

Spiral primer sets
(antisense sequences are underlined)

| | Sequence (5'-3') | SEQ ID NO: |
|---|---|---|
| Primer Combination 1 | | |
| E coli-SPR-O-F | GCCATCTCCTGATGACGC | 43 |
| E coli-SPR-O-R | ATTTACCGCAGCCAGACG | 44 |
| E coli-SPR-I-F1 | CTGACCCCAT | 45 |
| E coli-SPR-I-R2 | GAGAACCCGT | 46 |
| E coli-SPR-I-F3 | CCTCGTCGTG | 47 |
| Primer Combination 2 | | |
| E coli-SPR-O-F | GCCATCTCCTGATGACGC | 43 |
| E coli-SPR-I-R | ATTTACCGCAGCCAGACG | 44 |
| E coli-SPR-I-R1 | GTCAGATGGG | 48 |

TABLE 2-continued

Spiral primer sets
(antisense sequences are underlined)

|  | Sequence (5'-3') | SEQ ID NO: |
|---|---|---|
| E coli-SPR-I-F2 | TTCTCGGGCA | 49 |
| E coli-SPR-I-R3 | CGAGG<u>CACGA</u> | 50 |

The sequences and sizes of the primers were chosen so that their melting temperatures (Tm) fell within certain ranges. The primers were chosen such that their Tm values fell between 60 and 65° C., the optimal temperature for Bst polymerase. In addition, the outer primers were used at ¼-½ the concentration of the inner primers.

The efficiency of SPIDR depends on the size of the target DNA because one rate limiting step for amplification in this method is strand displacement DNA synthesis. We tested various sizes of target DNA and found that the best results could be obtained with 150 to 200 bp DNAs.

DNA polymerase was another consideration for efficient amplification. The best amplification was obtained with Bst polymerase and Pyrophage DNA polymerase. Pyrophage was able to conduct the reaction even at much higher temperatures (up to 80° C.) while Bst DNA polymerase was inactivated at temperatures higher than 70-72° C. Taq DNA polymerase (ABI) was not useful under the current conditions. Chemicals destabilizing the DNA helix were found to markedly elevate amplification efficiencies in SPIDR. The presence of 0.5-1.5 M betaine (N,N,N-trimethylglycine) increased target specificity with a significant reduction in amplification of irrelevant sequences.

SPIDR is highly sensitive and able to detect DNA at as few as 100 copies in the reaction mixture. In the absence of one of the outer primers or reversal of sequences of inner primers no significant amplification occurred with 10000 copies of the E. coli target (FIG. 9, lanes 3-4), indicating a strict requirement for recognition of distinct sequences and their orientation in the target DNA in SPIDR.

Besides gel electrophoresis, we also used two additional methods, visual inspection and spectrophotometry, to detect a positive reaction. Upon addition of the SYBR green I dye to tubes after the SPIDR reaction described in this Example, performed on Dengue virus, the color changed to yellowish green in a positive reaction and remained reddish orange (the color of the unbound dye) in the negative reactions.

All the experiments that were positive by gel electrophoresis were also positive by visual detection of color change (and vice versa). The visual detection of a positive reaction was further improved by using UV light from a conventional as well as a portable blue light transilluminator, which demonstrated a bright green fluorescence in positive reactions (FIG. 10, tube 1) while the negative control did not fluoresce (FIG. 10 tube 2). Finally, the positive reaction was also detected by a spectrophotometer in a real-time quantitative PCR machine in a quantitative manner.

Tests for other genomic targets, including West Nile Virus, were successfully performed by amplifying DNA/RNA isolated from organisms obtained from ATCC or collaborators using the methods described in this Example. Results compared favorably to other DNA amplification protocols such as PCR and LAMP.

The SPIDR process is shown herein to be a useful platform technology and is likely to find uses in a large number of applications that require DNA amplification and detection, and especially in molecular diagnostics as well as in point of care molecular assays. We developed SPIDR a novel method to amplify DNA with high specificity, efficiency and rapidity under isothermal conditions. This method employs a DNA polymerase and a set of 5 specially designed primers that recognize distinct sequences on the target DNA. An inner primer containing sequences of the sense and antisense strands of the target DNA initiates SPIDR. When combined with enzymes with RT activity, e.g., the enzymes from LUCIGEN it can also be used for RNA amplification without the need for separate reverse transcription step. The amplification products are specific and visible as a smear or ladder on a gel. SPIDR has comparable specificity and sensitivity to LAMP.

Example 3

SPIDR3 with Novel Internal Triplex Spiral Primers

A third variant of the SPIDR reaction is SPIDR3, essentially as depicted in FIG. 3. This variant utilizes outer primers, inner primers and triplex primers. SPIDR3 differs from SPIDR1 (base, e.g., as in FIG. 1) and SPIDR2 in the configuration of inner triplex primers. The outer primers are similar to SPIDR base. The two inner primers (1 forward (IF) and 1 reverse (IR)) are 10-20 base long primers located just inside of outer primers. The inner triplex primers are located inside the inner primers. Each novel SPIRAL3 Inner triplex primer (ITP) is of approximately 20-25 bases each and is a composite primer contains 3 distinct sequences corresponding to the sense and antisense and sense (or vice versa) sequences of the target DNA. For ease of explanation, the sequences (typically 20-22 nt) inside both ends of the target region for amplification in a DNA are designated antisense or sense (e.g., A+S+A). As an example a SP ITP-F may consist of 5-8 sense (S), 5-8 antisense (A) and 5-8 sense (S) bases; and the SP-ITP-R consists of 5-8 antisense (A), 5-8 sense (S) and 5-8 antisense (A) bases respectively (see, e.g., FIG. 3). Given this structure, the sequences of SP-ITP-F and SP-ITP-R were designed as follows (S-A-S bases and A-S-A bases), as shown in FIG. 10. The two outer primers consist of SP-O-F and the SP-O-R sequences (SP3-O-R is complementary to target DNA sequence) and are approximately 20-23 bases long. The outer primers play a role in priming in the first stage and the other inner primers are for self-priming in later stages. A DNA sample containing the target sequence and the 6 primers is mixed with the SPIDR reaction components is then initiated by addition of respective enzymes and carried out at 60-65° C. for 30 min to 1 h for the Bst DNA polymerase (with or without AMV for amplifying RNA or DNA targets respectively) and at 70-80° C. for 30 min to 1 h for Pyrophage Enzyme (LUCIGEN, for both RNA and DNA targets).

Reaction Mixture for SPIDR:

SPIDR3 was carried out in a total 20 µl reaction mixture containing 0.8 µM each ITP F and ITP-R, 0.4 µM each IF and IR, 0.2 µM each OF and OR, 400 µM each dNTP, 1 M betaine (Sigma), 20 mM Tris-HCl (pH 8.8), 10 mM KCl, 10 mM $(NH_4)_2SO_4$, 4 mM MgSO4, 0.1% Triton X-100 8 U Bst DNA polymerase large fragment (New England Biolabs*) and the specified amounts of double-stranded target DNA. The mixture was incubated at different temperatures of 60-80° C. for 30-60 minutes and the reaction products were visualized by a variety of methods.

In addition to above master mix conditions, we also evaluated other enzymes, including mixes of AMV reverse transcriptase and Bst Polymerase; and Pyrophage 3173 enzyme (LUCIGEN)

Figures 11, 12:
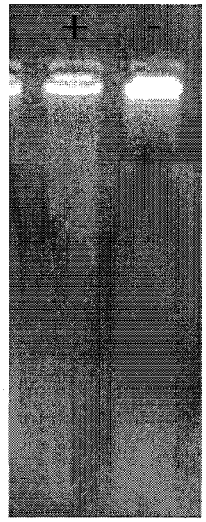
FIG. 12 is a photograph showing a gel in which the reaction products using SPIDR 3 primers, as shown in FIG. 11

The SPIDR3 primers were designed by visual inspection of target genomic sequences and checked by the software Primer3 (for various characteristics such as: Tm, self-complementarity, etc). The Primers and their genomic location on *Chlamydia* cryptic plasmid are shown in FIG. 11.

Aliquots of 5 μl of SPIDR products were electrophoresed in 2% agarose gels (0.5× TBE) followed by staining with SYBR Green I (Molecular Probes Inc.). They were also visualized by naked eye inspection addition of various DNA binding dyes to the reaction product mix after the completion of reaction. The dyes included SYBR green I dye, Eva Green dye and GR Safe dye at different concentrations. One microliter of SYBR green I dye (1:100 dilution of a 10,000× stock solution) was added to tubes containing SPIDR products.

In addition, we generated some of the amplicons of the SPIDR3 reaction products using labeled primers that were also detected on a lateral flow device (BESt Cassette) available from BioHelix. For this set of reactions, the products were generated using ITP primers that were labeled with FITC (ITP-F) and biotin (ITP-R). We present details of *Chlamydia trachomatis* detection by SPIDR3 below.

Amplification of Cloned *Chlamydia* DNA:

Cloning of *Chlamydia* DNA was performed to determine sensitivity. To determine the sensitivity of the SPIDR3 assay, we generated and quantitated a plasmid containing the target sequence amplified by PCR using outer primers as Forward and Reverse primers. The clone was quantified using UV spectrophotometry at 260 nm (SmartSpec 3000; Bio-Rad Laboratories, CA). A series of 10× dilutions, spanning 10 to $10^7$ copies/tube of the clone, was used to test the sensitivity of the SPIDR reactions. The SPIDR reaction was carried out at 65° C. for 45 min. Aliquots of 2 μl of the amplification products were mixed with 300 μl of 1/10 000 diluted original SYBR Green I in 10 mM Tris-HCl (pH 8.0), and 1 mM EDTA, incubated at room temperature for 30 min and quantified for fluorescent intensity with the SmartSpec 3000 spectrophotometer.

The specificity was tested by amplifying several non target bacteria and viruses and comparing the results with target amplification SPIDR3 Amplification of *Chlamydia* DNA as a Model:

In order to demonstrate the mechanism, the efficiency, the specificity and the ease of use of SPIDR3, we chose *Chlamydia* DNA as a model target DNA and prepared primers as shown in Table 3 and FIG. 11. The reaction was carried out at 65° C. with Bst DNA pol for 30 min to 1 h and the products were separated by agarose gel electrophoresis and also identified by naked eye visualization (FIG. 12). The SPIDR reaction produced many bands of different sizes from ~200 bp to the loading well (FIG. 12).

TABLE 3

*Chlamydia* SPIDR3 primers
(antisense sequences are underlined)

| Primer | Sequence | SEQ ID NO: |
|---|---|---|
| Chla SP3-OF | CATCGGTCAACGAAGAGGTT | 51 |
| Chla SP3-OR | CATCTTTGCGGTTGCGTGTCC | 52 |
| Chla SP3-ITP-F (F-R-F) | CGCACGTTGAGAGAAGCAGGAC | 53 |
| Chla SP3-ITP-R (R-F-R) | CGTTTGTAGACGGGAGACAGCGG | 54 |
| Chla SP3-IF | CTCAGACTCCGACATAATG | 55 |
| Chla SP3-IR | TTCCGGAGCGAGTTACGAAG | 56 |

Optimization of SPIDR3:

Since hybridization of the 6 primers to the target DNA in the initial step was critical for the efficiency of SPIDR, the sequences and sizes of the primers were chosen so that their melting temperatures (Tm) fell within certain ranges. The primers were chosen such that their Tm values fell between 60 and 65° C., the optimal temperature for Bst polymerase. In addition, the outer primers were used at ¼-½ the concentration of the inner primers.

The efficiency of SPIDR depends on the size of the target DNA because one rate limiting step for amplification in this method is strand displacement DNA synthesis. We tested various sizes of target DNA and found that the best results could be obtained with 150 to 200 bp DNAs.

DNA polymerase is another critical factor for efficient amplification. The best amplification was obtained with Bst polymerase and Pyrophage DNA polymerase. Taq DNA polymerase (ABI) was not useful under the current conditions. Chemicals destabilizing the DNA helix were found to markedly elevate amplification efficiencies in SPIDR. The presence of 0.5-1.5 M betaine (N,N,N-trimethylglycine) increased target specificity with a significant reduction in amplification of irrelevant sequences.

Sensitivity of SPIDR:

SPIDR is highly sensitive and able to detect DNA at as few as 10 copies in the reaction mixture. In the absence of one of the outer primers or reversal of sequences of inner primers no significant amplification occurred with 10000 copies of the target indicating a strict requirement for recognition of distinct sequences and their orientation in the target DNA in SPIDR.

Specificity of SPIDR:

Production of the bands depended on the presence of the primers, the template and DNA polymerase.

Sample Preparation:

No sample preparation was needed when urine, genital swabs, eye swabs or water were tested as biological or environmental samples. Blood samples required heating the sample at 95° C. and using the supernatant after precipitation of the proteins.

Example 4

Detection of SPIDR3 Amplification Product by Lateral Flow Device

SPIDR3 was performed essentially as described in Example 3, and the product was deposited in a lateral flow device essentially as described in FIGS. 13A and 13B. In the amplification reaction, the primer identified as Chla SP3-ITP-F was end-labeled with FITC and the primer Chla SP3-ITP-R was labeled with Biotin. Positive and negative samples were analyzed, and the results were as indicated in FIG. 13B, with a single line forming in the negative control (e.g., as in FIG. 13B, right) and two lines forming in the positive sample (e.g., as in FIG. 13B, left).

Example 5

Multiplexed SPIDR1 Assay Combined with Lateral Flow Device

SPIDR1 reactions were performed essentially as described in Example 1 for a mixed sample of *E. coli* and *Klebsiella* (*K. pneumoniae*) using the primers depicted in Table 1 for those organisms. The *E. coli* IR primer was end-labeled with FITC, the *Klebsiella* IR primer was labeled with digoxigenin, and both the *E. coli* and *Klebsiella* IF primers were labeled with biotin. Gold particles were labeled with streptavidin. The lateral flow devices were produced essentially as depicted in FIGS. 13A and 13B except the three lines of antibodies printed on the nitrocellulose were, in order from left to right in the context of FIG. 13A (iv), anti-FITC antibody, anti-digoxigenin antibody and anti-biotin antibody (all of which are commercially available). Gold particle-bound streptavidin is deposited in the device between the sample pad and the anti-FITC antibody. 20 µL of sample was deposited in the sample pad and the reaction was allowed to develop for five minutes. The lateral flow device was able to specifically distinguish positive reaction products for *E. coli* and *Klebsiella*. Positive control anti-biotin antibody binds biotin, yet still permits association of the biotin with gold-particle-bound streptavidin, thus acting as a positive control.

Whereas particular embodiments of this invention have been described above for purposes of illustration, it will be evident to those skilled in the art that numerous variations of the details of the present invention may be made without departing from the invention as defined in the appended claims.

I claim:

1. A method of identifying the presence of a target sequence in a nucleic acid sample, the method comprising:
   a. mixing in a reaction mixture ingredients comprising:
      i. a nucleic acid sample;
      ii. a first primer binding at a first binding site of a first strand of a nucleic acid target sequence having a 5' end and a 3' end;
      iii. a second primer binding at a second binding site to a complementary strand to the target sequence 5' to the first binding site with respect to the first strand;
      iv. an internal primer pair comprising a third primer binding to the first strand at a third binding site between the first binding site and the second binding site and a fourth primer binding to the complementary strand at a fourth binding site between the first binding site and the third binding site; and
      v. one or more spiral primers binding the target sequence between the third binding site and the fourth binding site, selected from:
         (i) a reverse internal spiral primer having a 5' portion and a 3' portion in which the 5' portion binds to the first strand and the 3' portion binds to the complementary strand;
         (ii) a forward internal spiral primer having a 5' portion and a 3' portion in which the 5' portion binds to the complementary strand and the 3' portion binds to the first strand;
         (iii) a reverse internal triplex spiral primer having a 5' portion, a 3' portion and a middle portion in which the 5' portion and the 3' portion binds the first strand and the middle portion binds the complementary strand; and
         (iv) a forward internal triplex spiral primer having a 5' portion, a 3' portion and a middle portion in which the 5' portion and the 3' portion binds the complementary strand and the middle portion binds the first strand;
      vi. a DNA polymerase; and
   b. incubating the reaction mixture at a temperature or combination of temperatures effective to produce one or more amplification products in a reaction mixture containing a nucleic acid comprising the target sequence.

2. The method of claim 1 in which the nucleic acid sample comprises the target sequence.

3. The method of claim 1 in which the one or more spiral primers of the reaction mixture comprises:
   a. a reverse internal spiral primer having a 5' portion and a 3' portion in which the 5' portion binds to the first strand and the 3' portion binds to the complementary strand; and
   b. a forward internal spiral primer having a 5' portion and a 3' portion in which the 5' portion binds to the complementary strand and the 3' portion binds to the first strand;
   in which the reverse internal spiral primer, and the forward internal spiral primer bind the target sequence between the third and fourth binding sites.

4. The method of claim 1 in which the one or more spiral primers of the reaction mixture comprises:
   a. a reverse internal triplex spiral primer having a 5' portion, a 3' portion and a middle portion in which the 5' portion and the 3' portion binds the first strand and the middle portion binds the complementary strand; and
   b. a forward internal triplex spiral primer having a 5' portion, a 3' portion and a middle portion in which the 5' portion and the 3' portion binds the complementary strand and the middle portion binds the first strand;
   in which the reverse internal triplex spiral primer and a forward internal triplex spiral primer bind the target sequence between the third and fourth binding sites.

5. The method of claim 4 in which the reverse internal triplex spiral primer binds the target sequence at a binding site 5' to a binding site of the forward triplex internal spiral primer.

6. A method of identifying the presence of a target sequence in a nucleic acid sample, the method comprising:
   a. mixing in a reaction mixture ingredients comprising:
      i. a nucleic acid sample;
      ii. a first primer binding at a first binding site of a first strand of a nucleic acid target sequence having a 5' end and a 3' end;
      iii. a second primer binding at a second binding site to a complementary strand to the target sequence 5' to the first binding site with respect to the first strand;
      iv. a reverse internal spiral primer having a 5' portion and a 3' portion in which the 5' portion binds to the first strand and the 3' portion binds to the complementary strand;
      v. a second reverse internal spiral primer having a 5' portion and a 3' portion in which the 5' portion binds to the first strand and the 3' portion binds to the complementary strand;
      vi. a forward internal spiral primer having a 5' portion and a 3' portion in which the 5' portion binds to the complementary strand and the 3' portion binds to the first strand;
      in which the reverse internal spiral primer, the second reverse internal spiral primer, and the forward internal spiral primer, bind the target sequence between the first and second binding sites; and
      vii. a DNA polymerase; and
   b. incubating the reaction mixture at a temperature or combination of temperatures effective to produce one or more amplification products in a reaction mixture containing a nucleic acid comprising the target sequence.

7. The method of claim 6 in which the forward internal spiral primer binds the target sequence at a binding site between binding sites of the reverse internal spiral primer and the second reverse internal spiral primer.

8. The method of claim 6 in which the 3' portion of one or more of the reverse internal spiral primer, the second reverse internal spiral primer and the forward internal spiral primer bind to the target sequence 3' to and immediately adjacent to the binding site of the 5' portion of the same primer.

9. A method of identifying the presence of a target sequence in a nucleic acid sample, the method comprising:
   a. mixing in a reaction mixture ingredients comprising:
      i. a nucleic acid sample;
      ii. a first primer binding at a first binding site of a first strand of a nucleic acid target sequence having a 5' end and a 3' end;
      iii. a second primer binding at a second binding site to a complementary strand to the target sequence 5' to the first binding site with respect to the first strand;
      iv. a reverse internal triplex spiral primer having a 5' portion, a 3' portion, and a middle portion in which the 5' portion and the 3' portion binds the first strand and the middle portion binds the complementary strand;
      v. a forward internal triplex spiral primer having a 5' portion, a 3' portion, and a middle portion in which the 5' portion and the 3' portion binds the complementary strand and the middle portion binds the first strand;
   in which the reverse internal triplex spiral primer and a forward internal triplex spiral primer bind the target sequence between the first and second binding sites;
      vi. a DNA polymerase; and
   b. incubating the reaction mixture at a temperature or combination of temperatures effective to produce one or more amplification products in a reaction mixture containing a nucleic acid comprising the target sequence.

10. The method of claim 9 in which the reverse internal triplex spiral primer binds the target sequence at a binding site 5' to a binding site of the forward triplex internal spiral primer.

11. The method of claim 1 in which the nucleic acid sample comprises RNA and either the DNA polymerase has reverse transcriptase activity or the reaction mixture further comprises a reverse transcriptase.

12. The method of claim 1 in which the 3' portion of the third primer binds to the target strand 3' to and immediately adjacent to the binding site of the 5' portion of the third primer.

13. The method of claim 1 in which the amplification is isothermic, using a strand-displacing polymerase.

14. The method of claim 1 in which the method is multiplexed such that a second nucleic acid is amplified in the reaction mixture.

15. The method of claim 1 in which the target sequence is a sequence of a pathogen.

16. The method of claim 15 in which the pathogen is selected from the group consisting of influenza A virus, influenza B virus, West Nile virus, HIV virus, Dengue virus, *Klebsiella, E. coli* and *Chlamydia*.

17. The method of claim 1, in which one or more inner primer comprises a detectable tag.

* * * * *

```
                          SEQUENCE LISTING

<160> NUMBER OF SEQ ID NOS: 57

<210> SEQ ID NO 1
<211> LENGTH: 344
<212> TYPE: DNA
<213> ORGANISM: Human immunodeficiency virus

<400> SEQUENCE: 1
gaaggctttt agcccagaag taatacccat gttttcagcg ttatcagaag gagccacccc      60
acaagattta aacaccatgc taaacacagt gggggggacat caagcagcca tgcaaatatt     120
aaaagatacc atcaatgaag aggctgcaga atgggataga ttacatccag tacatgcagg     180
gcctattgca ccaggccaaa tgagagaacc aaggggaagt gacatagcag gaactactag     240
taacctacag gaacaaatag catggatgac gagtaaccca cctgttccag taggagacat     300
ctataaaaga tggataattc tgggattaaa taaaatagta agaa                      344

<210> SEQ ID NO 2
<211> LENGTH: 324
<212> TYPE: DNA
<213> ORGANISM: Dengue virus

<400> SEQUENCE: 2
accgtgctgc ctgtagctcc gccaataacg ggaggcgtta aattcccagg gaggccatgc      60
gccacggaag ctgtgcgcgt ggcatattgg actagcggtt agaggagacc cctcccatca     120
ccaacaaaac gcagcaaaaa aggggcccg aagccaggag gaagctgtac tcctggtgga      180
aggactagag gttagaggag accccccaa cacaaaaaca gcatattgac gctgggaaag     240
accagagatc ctgctgtctc tacaacatca atccaggcac agagcgccgc gagatggatt     300
ggtgttgttg atccaacagg ttct                                             324

<210> SEQ ID NO 3
<211> LENGTH: 350
<212> TYPE: DNA
<213> ORGANISM: West Nile virus

<400> SEQUENCE: 3
aagcttggag aatatggaga ggtgacagtg gactgtgaac cacggtcagg gattgacacc      60
aatgcatact acgtgatgac tgttggaaca aagacgttct tggtccatcg tgagtggttc      120
```

-continued atggacctca acctcccttg gagcagtgct ggaagtactg tgtggaggaa cagagagacg 180
ttaatggagt ttgaggaacc acacgccacg aagcagtctg tgatagcatt gggctcacaa 240
gagggagctc tgcatcaagc tttggctgga gccattcctg tggaattttc aagcaacact 300
gtcaagttga cgtcgggtca tttgaagtgt agagtgaaga tggaaaaatt 350

<210> SEQ ID NO 4
<211> LENGTH: 355
<212> TYPE: DNA
<213> ORGANISM: Influenza A virus

<400> SEQUENCE: 4
atattgaaag atgagtcttc taaccgaggt cgaaacgtac gttctctcta tcgtcccgtc 60
aggccccctc aaagccgaga tcgcacagag acttgaagat gtctttgctg gaaagaacac 120
cgatcttgag gctctcatgg aatggctaaa gacaagaccg atcctgtcac ctctgactaa 180
ggggatttta ggatttgtgt tcacgctcac cgtgcccact gagcgaggac tgcatcgtac 240
actctttgtc caaaatgccc ttaatgggaa tggggatcca aataatatgg acagagcagt 300
taaactgtat agaaagctta agagggagat aacattccat ggggccaaag aaata 355

<210> SEQ ID NO 5
<211> LENGTH: 442
<212> TYPE: DNA
<213> ORGANISM: Influenza B virus

<400> SEQUENCE: 5
tatgtcgctg tttggagaca caattgccta cctgctttca ttgacagaag atggagaagg 60
caaagcagaa ctagcagaaa aattacactg ttggtttggt gggaaagaat ttgacctaga 120
ctctgccttg gaatggataa aaaacaaaag atgcttaact gatatacaaa aagcactaat 180
tggtgcctct atatgctttt taaaacccaa agaccaggaa agaaaaagaa gattcatcac 240
agagccctta tcaggaatgg gaacaacagc aacaaaaaag aaaggcctga ttctggctga 300
gagaaaaatg agaagatgtg tgagctttca tgaagcattt gaaatagcag aaggccatga 360
aagctcagcg ctactatact gtctcatggt catgtacctg aatcctggaa attattcaat 420
gcaagtaaaa ctaggaacgc tc 442

<210> SEQ ID NO 6
<211> LENGTH: 389
<212> TYPE: DNA
<213> ORGANISM: Escherichia coli

<400> SEQUENCE: 6
gaaacaccat accaacgcca cgttctgctg gcggagtgtc attcatccgt ttctcaccga 60
tgaacaggtc gccgctggtg atcgtctcaa gcccggcaat catgcgcagt aaagtcgatt 120
taccgcagcc agacggtccg acaaacacca cgaattcacc ttcatggata tcgagattga 180
tatctttcga taccacgacc tcgccccagg ctttcgttac attttgcagc tgtacgctcg 240
ccatgccctt ctccctttgt aacaacctgt catcgacagc aacattcatg atgggctgac 300
tatgcgtcat caggagatgg cttaaatcct ccacccccta gctttttat gggggaggag 360 gcgggaggat gagaacgcgg cttctgtga 389

<210> SEQ ID NO 7
<211> LENGTH: 222
<212> TYPE: DNA
<213> ORGANISM: Klebsiella pneumoniae

<400> SEQUENCE: 7

| aaactgattg gtctgccggc gccggtaggc atgctgttcc tcgcggtact gttaaagctg | 60 |
| gctaacgtgg tgtctccgcg tctgcaggag gggtcgcaga tggtgtataa attcttccgc | 120 |
| accgcggtca cctacccgat cctctttgcc gtcggcgtgg cgatcactcc gtggcaggaa | 180 |
| ctggtaaacg ccttcacttt aaccaacctg ctggtgatcg tc | 222 |

<210> SEQ ID NO 8
<211> LENGTH: 957
<212> TYPE: DNA
<213> ORGANISM: Chlamydia trachomatis

<400> SEQUENCE: 8

| aagttagacg aaattttgtc tttgcgcaca gacgatctat ttttttgcatc caatcagatt | 60 |
| tcctttcgca ttaaaaaaag acagaataaa gaaaccaaaa ttctaatcac atttcctatc | 120 |
| agcttaatgg aggagttgca aaatacact tgtgggagaa atgggagagt atttgtttct | 180 |
| aaaataggga ttcctgtaac aacaagtcag gttgcgcata tttttaggct tgcagagttc | 240 |
| tatagtgcta tgaaaataaa aattactcct agagtacttc gtgcaagcgc tttgattcat | 300 |
| ttaaagcaaa taggattaaa agatgaggaa atcatgcgta tttcctgtct ttcatcgaga | 360 |
| caaagtgtgt gttcttattg ttctggggaa gaggtaagtc ctctagtaca aacaccccca | 420 |
| atattgtgat ataattaaaa ttatattcat attctgttgc cagaaaaaac acttttaggc | 480 |
| tatattagag ccaatcttct ttgaagcgtt gtcttctcga aagatttat cgtacgcaaa | 540 |
| tatcatcttt gcggttgcgt gtcctgtgac cttcattatg tcggagtctg agcaccctag | 600 |
| gcgtttgtac tccgtcacag cggttgctcg aagcacgtgc ggggttatct taaagggat | 660 |
| tgcagcttgt agtcctgctt gagagaacgt gcgggcgatt tgccttaacc ccaccatttt | 720 |
| tccggagcga gttacgaaga caaaacctct tcgttgaccg atgtactctt gtagaaagtg | 780 |
| cataaacttc tgaggataag ttataataat cctctttct gtctgacggt tcttaagctg | 840 |
| ggagaaagaa atggtagctt gttggaaaca atctgactta atctccaagc ttaagacttc | 900 |
| agaggagcgt ttacctcctt ggagcattgt ctgggcgatc aaccaatccc gggcatt | 957 |

<210> SEQ ID NO 9
<211> LENGTH: 204
<212> TYPE: DNA
<213> ORGANISM: Escherichia coli

<400> SEQUENCE: 9

| gccatctcct gatgacgcat agtcagccca tcatgaatgt tgctgtcgat gacaggttgt | 60 |
| tacaaaggga aagggcatg gcgagcgtac agctgcaaaa tgtaacgaaa gcctggggcg | 120 |
| aggtcgtggt atcgaaagat atcaatctcg atatccatga aggtgaattc gtggtgtttg | 180 |
| tcggaccgtc tggctgcggt aaat | 204 |

<210> SEQ ID NO 10
<211> LENGTH: 243
<212> TYPE: DNA
<213> ORGANISM: Chlamydia trachomatis

<400> SEQUENCE: 10

| tgcactttct acaagagtac atcggtcaac gaagaggttt tgtcttcgta actcgctccg | 60 |
| gaaaatggt ggggttaagg caaatcgccc gcccgcacgt tctctcaagc aggactacaa | 120 |
| gctgcaatcc cttttaagat aaccccgcac gtgcttcgag caaccgctgt gacggagtac | 180 |

```
aaacgcctag ggtgctcaga ctccgacata atgaaggtca caggacacgc aaccgcaaag      240
atg                                                                    243

<210> SEQ ID NO 11
<211> LENGTH: 25
<212> TYPE: DNA
<213> ORGANISM: Influenza A virus

<400> SEQUENCE: 11
gagtcttcta accgaggtcg aaacg                                             25

<210> SEQ ID NO 12
<211> LENGTH: 23
<212> TYPE: DNA
<213> ORGANISM: Influenza A virus

<400> SEQUENCE: 12
ttcccattga gggcattttg gac                                               23

<210> SEQ ID NO 13
<211> LENGTH: 21
<212> TYPE: DNA
<213> ORGANISM: Influenza A virus

<400> SEQUENCE: 13
gttctttcca gcaaagacat c                                                 21

<210> SEQ ID NO 14
<211> LENGTH: 16
<212> TYPE: DNA
<213> ORGANISM: Influenza A virus

<400> SEQUENCE: 14
gtgttcacgc tcaccg                                                       16

<210> SEQ ID NO 15
<211> LENGTH: 21
<212> TYPE: DNA
<213> ORGANISM: Influenza B virus

<400> SEQUENCE: 15
tatgtcgctg tttggagaca c                                                 21

<210> SEQ ID NO 16
<211> LENGTH: 22
<212> TYPE: DNA
<213> ORGANISM: Influenza B virus

<400> SEQUENCE: 16
gagcgttcct agttttactt gc                                                22

<210> SEQ ID NO 17
<211> LENGTH: 18
<212> TYPE: DNA
<213> ORGANISM: Influenza B virus

<400> SEQUENCE: 17
ccaaggcaga gtctggtc                                                     18

<210> SEQ ID NO 18
<211> LENGTH: 19
<212> TYPE: DNA
<213> ORGANISM: Influenza B virus
```

```
<400> SEQUENCE: 18
gaaatagcag aaggccatg                                          19

<210> SEQ ID NO 19
<211> LENGTH: 21
<212> TYPE: DNA
<213> ORGANISM: West Nile virus

<400> SEQUENCE: 19
gggattgaca ccaatgcata c                                       21

<210> SEQ ID NO 20
<211> LENGTH: 20
<212> TYPE: DNA
<213> ORGANISM: West Nile virus

<400> SEQUENCE: 20
ccatcttcac tctacacttc                                         20

<210> SEQ ID NO 21
<211> LENGTH: 19
<212> TYPE: DNA
<213> ORGANISM: West Nile virus

<400> SEQUENCE: 21
agcactgctc caagggagg                                          19

<210> SEQ ID NO 22
<211> LENGTH: 21
<212> TYPE: DNA
<213> ORGANISM: West Nile virus

<400> SEQUENCE: 22
gcatcaagct ttggctggag c                                       21

<210> SEQ ID NO 23
<211> LENGTH: 20
<212> TYPE: DNA
<213> ORGANISM: Human immunodeficiency virus

<400> SEQUENCE: 23
raaggcttty agcccagaar                                         20

<210> SEQ ID NO 24
<211> LENGTH: 20
<212> TYPE: DNA
<213> ORGANISM: Human immunodeficiency virus

<400> SEQUENCE: 24
tctccyactg grayaggtgg                                         20

<210> SEQ ID NO 25
<211> LENGTH: 20
<212> TYPE: DNA
<213> ORGANISM: Human immunodeficiency virus

<400> SEQUENCE: 25
taaatcttgt ggggtggctc                                         20

<210> SEQ ID NO 26
<211> LENGTH: 25
<212> TYPE: DNA
<213> ORGANISM: Human immunodeficiency virus
```

```
<400> SEQUENCE: 26
catagcagga actactagta ccctt                                        25

<210> SEQ ID NO 27
<211> LENGTH: 18
<212> TYPE: DNA
<213> ORGANISM: Dengue virus

<400> SEQUENCE: 27
cwggcctgta gctccryc                                                18

<210> SEQ ID NO 28
<211> LENGTH: 23
<212> TYPE: DNA
<213> ORGANISM: Dengue virus

<400> SEQUENCE: 28
gaacctgttg rwtcaacarc acc                                          23

<210> SEQ ID NO 29
<211> LENGTH: 20
<212> TYPE: DNA
<213> ORGANISM: Dengue virus

<400> SEQUENCE: 29
gggaggggtc tcctctaacc                                              20

<210> SEQ ID NO 30
<211> LENGTH: 22
<212> TYPE: DNA
<213> ORGANISM: Dengue virus

<400> SEQUENCE: 30
agaccagaga tcctgctgtc tc                                           22

<210> SEQ ID NO 31
<211> LENGTH: 20
<212> TYPE: DNA
<213> ORGANISM: Escherichia coli

<400> SEQUENCE: 31
gccgcgttct catcctcccg                                              20

<210> SEQ ID NO 32
<211> LENGTH: 23
<212> TYPE: DNA
<213> ORGANISM: Escherichia coli

<400> SEQUENCE: 32
ctggtgatcg tctcaagccc ggc                                          23

<210> SEQ ID NO 33
<211> LENGTH: 18
<212> TYPE: DNA
<213> ORGANISM: Escherichia coli

<400> SEQUENCE: 33
cattttgcag ctgtacgc                                                18

<210> SEQ ID NO 34
<211> LENGTH: 20
<212> TYPE: DNA
<213> ORGANISM: Escherichia coli
```

<400> SEQUENCE: 34
ctggggcgag gtcgtggtat                                         20

<210> SEQ ID NO 35
<211> LENGTH: 19
<212> TYPE: DNA
<213> ORGANISM: Klebsiella pneumoniae

<400> SEQUENCE: 35
aaactgattg gtctgccgg                                          19

<210> SEQ ID NO 36
<211> LENGTH: 19
<212> TYPE: DNA
<213> ORGANISM: Klebsiella pneumoniae

<400> SEQUENCE: 36
gacgatcacc agcaggttg                                          19

<210> SEQ ID NO 37
<211> LENGTH: 16
<212> TYPE: DNA
<213> ORGANISM: Klebsiella pneumoniae

<400> SEQUENCE: 37
gcagacgcgg agacac                                             16

<210> SEQ ID NO 38
<211> LENGTH: 16
<212> TYPE: DNA
<213> ORGANISM: Klebsiella pneumoniae

<400> SEQUENCE: 38
cttccgcacc gcggtc                                             16

<210> SEQ ID NO 39
<211> LENGTH: 20
<212> TYPE: DNA
<213> ORGANISM: Chlamydia trachomatis

<400> SEQUENCE: 39
catcggtcaa cgaagaggtt                                         20

<210> SEQ ID NO 40
<211> LENGTH: 21
<212> TYPE: DNA
<213> ORGANISM: Chlamydia trachomatis

<400> SEQUENCE: 40
catctttgcg gttgcgtgtc c                                       21

<210> SEQ ID NO 41
<211> LENGTH: 15
<212> TYPE: DNA
<213> ORGANISM: Chlamydia trachomatis

<400> SEQUENCE: 41
gccttaaccc cacca                                              15

<210> SEQ ID NO 42
<211> LENGTH: 20
<212> TYPE: DNA
<213> ORGANISM: Chlamydia trachomatis

```
<400> SEQUENCE: 42
ataaccccgc acgtgcttcg                                             20

<210> SEQ ID NO 43
<211> LENGTH: 18
<212> TYPE: DNA
<213> ORGANISM: Escherichia coli

<400> SEQUENCE: 43
gccatctcct gatgacgc                                               18

<210> SEQ ID NO 44
<211> LENGTH: 18
<212> TYPE: DNA
<213> ORGANISM: Escherichia coli

<400> SEQUENCE: 44
atttaccgca gccagacg                                               18

<210> SEQ ID NO 45
<211> LENGTH: 10
<212> TYPE: DNA
<213> ORGANISM: Artificial Sequence
<220> FEATURE:
<223> OTHER INFORMATION: Spiral primer for SPIDR2

<400> SEQUENCE: 45
ctgaccccat                                                        10

<210> SEQ ID NO 46
<211> LENGTH: 10
<212> TYPE: DNA
<213> ORGANISM: Artificial Sequence
<220> FEATURE:
<223> OTHER INFORMATION: Spiral primer for SPIDR2

<400> SEQUENCE: 46
gagaacccgt                                                        10

<210> SEQ ID NO 47
<211> LENGTH: 10
<212> TYPE: DNA
<213> ORGANISM: Artificial Sequence
<220> FEATURE:
<223> OTHER INFORMATION: Spiral primer for SPIDR2

<400> SEQUENCE: 47
cctcgtcgtg                                                        10

<210> SEQ ID NO 48
<211> LENGTH: 10
<212> TYPE: DNA
<213> ORGANISM: Artificial Sequence
<220> FEATURE:
<223> OTHER INFORMATION: Spiral primer for SPIDR2

<400> SEQUENCE: 48
gtcagatggg                                                        10

<210> SEQ ID NO 49
<211> LENGTH: 10
<212> TYPE: DNA
<213> ORGANISM: Artificial Sequence
<220> FEATURE:
<223> OTHER INFORMATION: Spiral primer for SPIDR2
```

```
<400> SEQUENCE: 49
ttctcgggca                                                          10

<210> SEQ ID NO 50
<211> LENGTH: 10
<212> TYPE: DNA
<213> ORGANISM: Artificial Sequence
<220> FEATURE:
<223> OTHER INFORMATION: Spiral primer for SPIDR2

<400> SEQUENCE: 50
cgaggcacga                                                          10

<210> SEQ ID NO 51
<211> LENGTH: 20
<212> TYPE: DNA
<213> ORGANISM: Chlamydia trachomatis

<400> SEQUENCE: 51
catcggtcaa cgaagaggtt                                               20

<210> SEQ ID NO 52
<211> LENGTH: 21
<212> TYPE: DNA
<213> ORGANISM: Chlamydia trachomatis

<400> SEQUENCE: 52
catctttgcg gttgcgtgtc c                                             21

<210> SEQ ID NO 53
<211> LENGTH: 22
<212> TYPE: DNA
<213> ORGANISM: Artificial Sequence
<220> FEATURE:
<223> OTHER INFORMATION: Spiral primer for SPIDR3

<400> SEQUENCE: 53
cgcacgttga gagaagcagg ac                                            22

<210> SEQ ID NO 54
<211> LENGTH: 23
<212> TYPE: DNA
<213> ORGANISM: Artificial Sequence
<220> FEATURE:
<223> OTHER INFORMATION: Spiral primer for SPIDR3

<400> SEQUENCE: 54
cgtttgtaga cgggagacag cgg                                           23

<210> SEQ ID NO 55
<211> LENGTH: 19
<212> TYPE: DNA
<213> ORGANISM: Chlamydia trachomatis

<400> SEQUENCE: 55
ctcagactcc gacataatg                                                19

<210> SEQ ID NO 56
<211> LENGTH: 20
<212> TYPE: DNA
<213> ORGANISM: Chlamydia trachomatis

<400> SEQUENCE: 56
ttccggagcg agttacgaag                                               20
```

```
<210> SEQ ID NO 57
<211> LENGTH: 16
<212> TYPE: RNA
<213> ORGANISM: Artificial Sequence
<220> FEATURE:
<223> OTHER INFORMATION: Oligonucleotide

<400> SEQUENCE: 57
agaggagaga gagaga                                                    16
```